(12) United States Patent
Cases et al.

US007862819B2

(10) Patent No.: US 7,862,819 B2
(45) Date of Patent: Jan. 4, 2011

(54) DIACYLGLYCEROL O-ACYLTRANSFERASE 2α (DGAT2α)

(75) Inventors: Sylvaine Cases, Belmont, CA (US); Robert V. Farese, San Francisco, CA (US); Scot J. Stone, Fairfield, CA (US); Ping Zhou, Walnut Creek, CA (US)

(73) Assignee: The J. David Gladstone Institutes, Irvine, CA (US)

( * ) Notice: Subject to any disclaimer, the term of this patent is extended or adjusted under 35 U.S.C. 154(b) by 563 days.

(21) Appl. No.: 10/446,441

(22) Filed: May 27, 2003

(65) Prior Publication Data

US 2003/0202968 A1 Oct. 30, 2003

Related U.S. Application Data

(62) Division of application No. 09/794,715, filed on Feb. 26, 2001, now abandoned.

(60) Provisional application No. 60/271,307, filed on Feb. 23, 2001.

(51) Int. Cl.
*A61K 39/395* (2006.01)
*C12N 9/10* (2006.01)
*C12N 15/09* (2006.01)

(52) U.S. Cl. ............... 424/146.1; 435/7.1; 435/193; 435/69.2; 530/387.1; 530/388.1; 530/387.9; 424/130.1; 424/141.1

(58) Field of Classification Search ............ 435/193, 435/69.1; 514/789; 530/350, 387.1
See application file for complete search history.

(56) References Cited

U.S. PATENT DOCUMENTS

| | | | |
|---|---|---|---|
| 6,100,077 A | 8/2000 | Sturley et al. | |
| 2003/0170691 A1 | 9/2003 | Rosana et al. | |

FOREIGN PATENT DOCUMENTS

| | | | |
|---|---|---|---|
| WO | WO 98/55631 | | 12/1998 |
| WO | WO 99/67268 | | 12/1999 |
| WO | WO 99/67403 | | 12/1999 |
| WO | WO 00/01713 | | 1/2000 |
| WO | WO 00/05367 | | 2/2000 |
| WO | WO 00/12708 | * | 3/2000 |
| WO | WO 00/12708 A2 | | 3/2000 |
| WO | WO 00/32756 A2 | | 6/2000 |
| WO | WO 00/32756 A3 | | 6/2000 |
| WO | WO 00/32793 A2 | | 6/2000 |
| WO | WO 00/32793 A3 | | 6/2000 |
| WO | WO 00/36114 A1 | | 6/2000 |
| WO | WO 99/47655 | * | 9/2000 |
| WO | WO 00/60095 A2 | | 10/2000 |
| WO | WO 00/60095 A3 | | 10/2000 |
| WO | WO 00/66749 | | 11/2000 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

Zhu et al., Niacin inhibits activity of Diacylglycerol acyltransferase (DGAT), a key enzyme for Triglyceride synthesis in HEPG2 Cells, Journal of Investigative Medicine, vol. 48, No. 2, pp. 206A, Mar. 2000.*

Ganji et al., "Niacin noncompetitively inhibits DGAT2 but not DGAT1 activity in HepG2 cells", Journal of Lipid Research, vol. 45, pp. 1835-1845, 2004.*

Cases et al. (1998) "Identification of a gene encoding an acyl CoA:diacylglycerol acyltransferase, a key enzyme in triacylglycerol synthesis." *Proc. Natl. Acad. Sci. USA*, vol. 95:13018-13023.

Oelkers et al. (1998) "Characterization of Two Human Genes Encoding Acyl Coenzyme A: Cholesterol Acyltransferase-related Enzymes." *J. Biol. Chem.*, vol. 273(41):26765-26771.

Smith et al. (2000) "Obesity resistance and multiple mechanisms of triglyceride synthesis in mice lacking Dgat." *Nature Genetics*, vol. 25:87-90.

Database EMBL Online! EBI, Dec. 1, 2001, "Diacylglycerol acytransferase 2 (hypothetical protein)", retrieved from EMBL, Database accession No. Q96PD7, XP002285959, see sequence.

Database EMBL Online! EBI; Oct. 8, 2001, "Homo sapiens diacylglycerol O-acyltransferase homolog 2 (mouse), mRNA, (cDNA clone MGC: 17861 IMAGE:3903313)" retrieved from EMBL Database accession No. BC015234, XP002285960, see sequence.

Database EMBL Online! EBI; Jun. 1, 2001, "0610010B06Rik protein (Diacylglycerol acyltransferase 2")" retrieved from EMBL, Database accession No. Q9DCV3, XP002285961.

Farese, Robert V. Jr. et al., "Triglyceride synthesis: Insights from the cloning of diacylglycerol acyltransferase" Current Opinion in Lipidology, vol. 11, No. 3, Jun. 2000, pp. 229-234.

Cases, S et al. "Cloning of DGAT2, a second mammalian diacylglycerol acyltransferase, and related family members" Journal of Biological Chemistry, American Chemical Society of Biological Chemists, Baltimore, MD, US, vol. 276, No. 42, Oct. 19, 2001, pp. 38870-38876, XP002199715.

Lehner, Richard et al., "Biosynthesis of triacylglycerols" Progress in Lipid Research, Pergamon Press, Paris, FR, vol. 35, No. 2, 1996, pp. 169, 201a, XP002262929, ISSN: 0163-7827, the whole document, in particular, pp. 179-190.

Database EMBL EBI; Feb. 9, 2001. "Mus musculus adult male testis cDNA, RIKEN full-length enriched library, clone:4933405B12 product:diacylglyerol o-acyltransferase 2, full insert sequence." retrieved from EMBL accession No. AKO16660.

Database EMBL [Onine] Feb. 8, 2001, "Musmusculus adult male kidney cDNA, RIKEN full-length enriched library, clone:0610010B06 product:diacylglycerol O-acyltransferase 2, full insert sequence." retrieved from EBI accession No. EMBL:AK002443 Database accession No. AK002443.

* cited by examiner

*Primary Examiner*—Richard G Hutson
(74) *Attorney, Agent, or Firm*—Paula A. Borden; Bozicevic, Field & Francis LLP

(57) ABSTRACT

Nucleic acid compositions encoding mammalian DGAT2α polypeptide products with diglyceride acyltransferase activity, as well as the mammalian DGAT2α polypeptide products encoded thereby and methods for producing the same, are provided. The subject DGAT2α polypeptide and nucleic acid compositions find use in a variety of applications, including research, diagnostic, and therapeutic agent screening applications, as well as in treatment therapies and in the production of triacylglycerols.

2 Claims, 12 Drawing Sheets

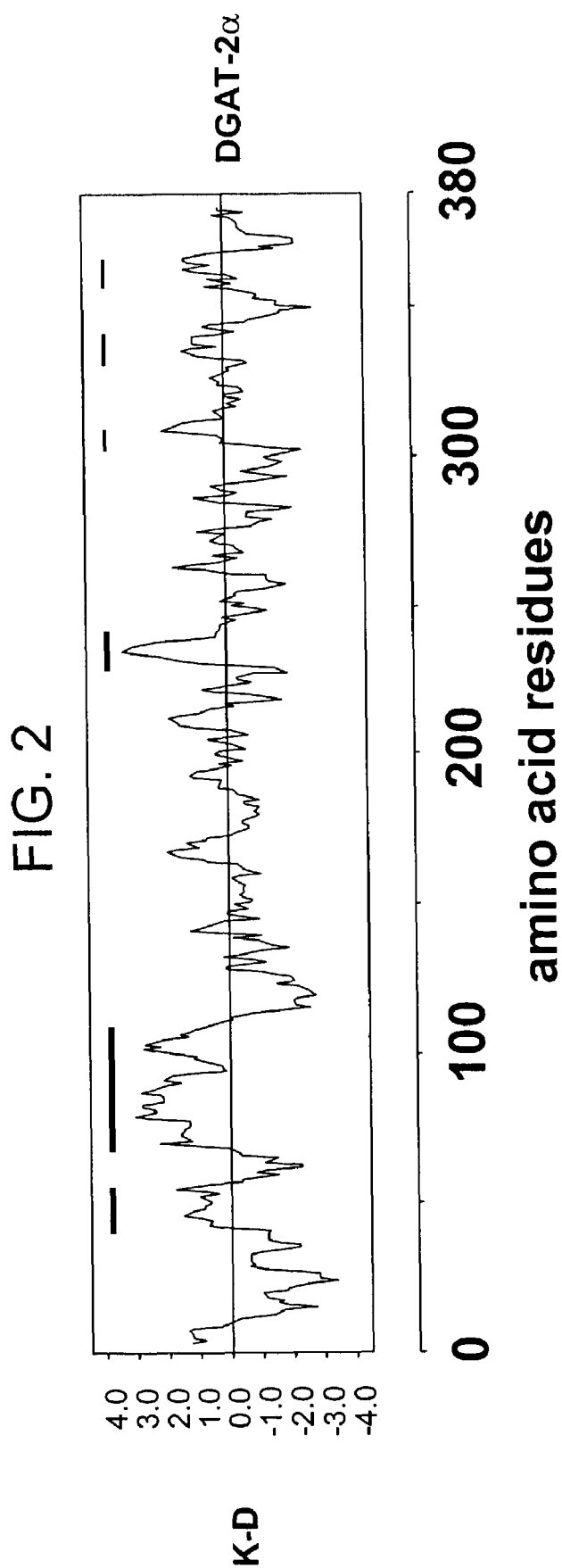

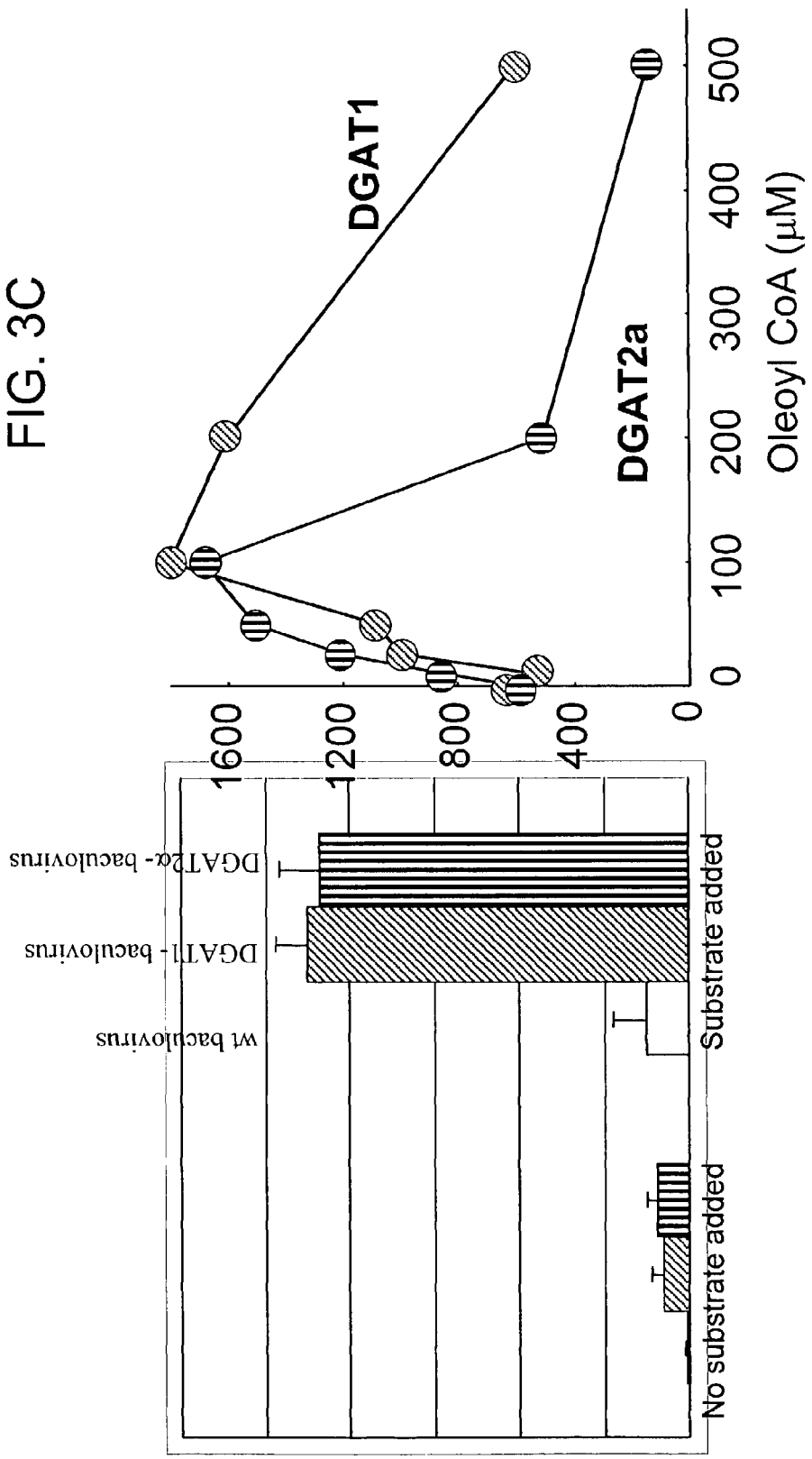

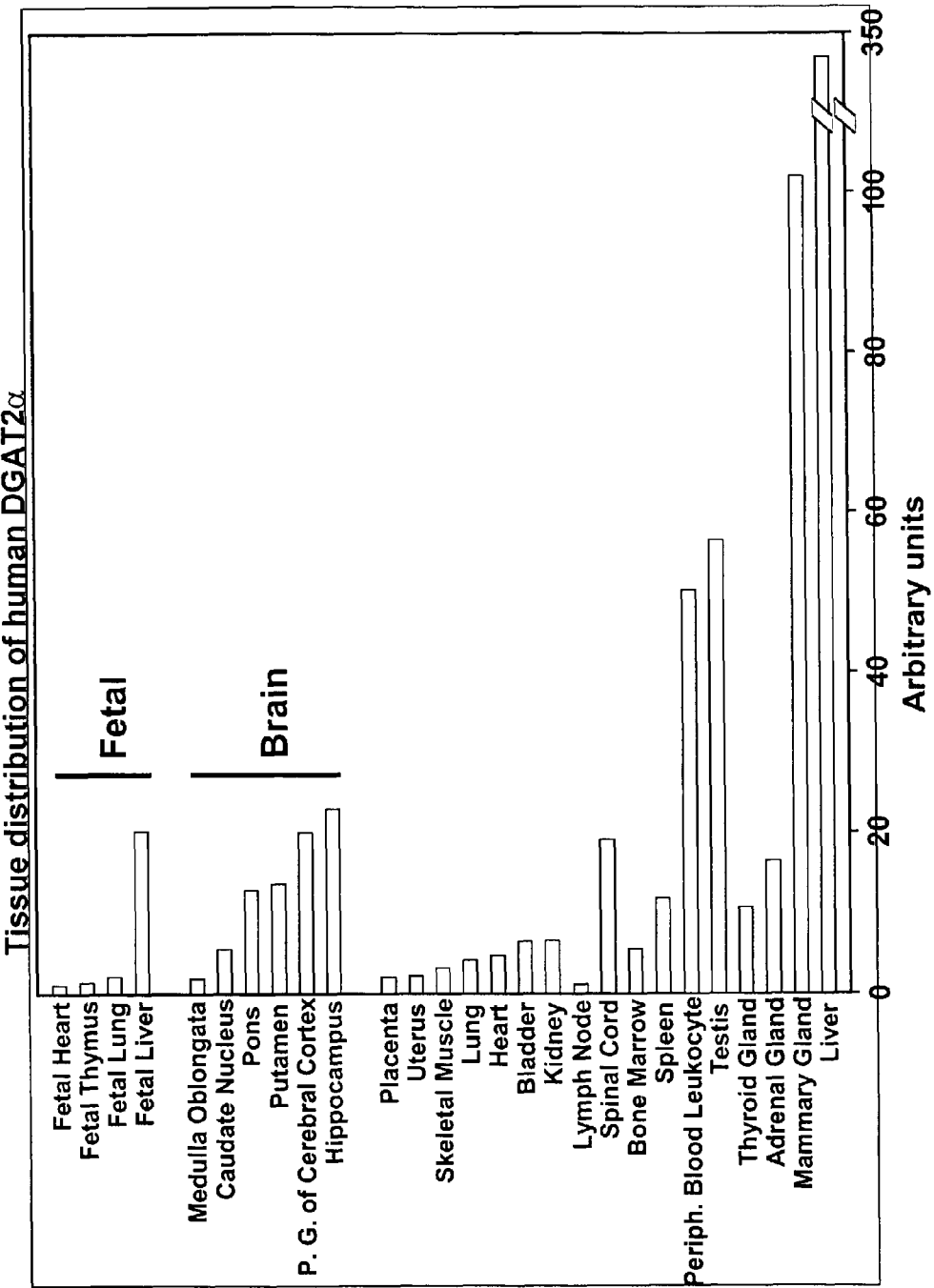

FIG. 6A

Mouse DGAT2α amino acid sequence

MKTLIAAYSGVLRGERRAELPAAKNKNKGSALSREGSGRWGTCSSILSALQDIFSVTWLNRSKVEKQLQV
ISVLQWVLSFLVLGVACSVILMYTFCTDCWLIAVLYFTWLAFDWNTPKKGGRRSQWVRNWAVWRYFRDYF
PIQLVKTHNLLTTRNYIFGYHPHGIMGLGAFCNFSTEATEVSKKFPGIRPYLATLAGNFRMPVLREYLMS
GGICLVNRDTIDYLLSKNGSGNAIIIVVGGAAESLSSMPGKNAVTLKNRKGFVKLALRHGADLVPTYSFG
ENEVYKQVIFEEGSWGRWVKKFQKYIGFAPCIFHGRGLFSSDTWGLVPYSKPITTVVGEPITVPKLEHPT
QKDIDLYHAMYMEALVKLFDNHKTKFGLPETEVLEVN (SEQ ID NO:04)

FIG. 6B

Mouse DGAT2α nucleic acid sequence

ATGAAGACCCTCATCGCCGCCTACTCCGGGGTCCTGCGGGGTGAGCGTCGGGCGGAAGCTGCCCGCAGCG
AAAACAAGAATAAAGGATCTGCCCTGTCACGCGAGGGGTCTGGGCGATGGGGCACTGGCTCCAGCATCCT
CTCAGCCCTCCAAGACATCTTCTCTGTCACCTGGCTCAACAGATCYAAGGTGGAAAAACAGCTGCAGGTC
ATCTCAGTACTACAATGGGTCCTATCCTTCCTGGTGCTAGGAGTGGCCTGCAGTGTCATCCTCATGTACA
CCTTCTGCACAGACTGCTGGCTGATAGCTGTGCTCTACTTCACCTGGCTGGCATTTGACTGGAACACGCC
CAAGAAAGGTGGCAGGAGATCGCAGTGGGTGCGAAACTGGGCCGTGTGGCGCTACTTCCGAGACTACTTT
CCCATCCAGCTGGTGAAGACACACAACCTGCTGACCACCAGGAACTATATCTTTGGATACCACCCCCATG
GCATCATGGGCCTGGGTGCCTTCTGTAACTTCAGCACAGAGGCTACTGAAGTCAGCAAGAAGTTTCCTGG
CATAAGGCCCTATTTGGCTACGTTGGCYGGTAACTTCCGGATGCCTGTGCTTCGCGAGTACCTGATGTCT
GGAGGCATCTGCCCTGTCAACCGAGACACCATAGACTACTTGCTCTCCAAGAATGGGAGTGGCAATGCTA
TCATCATCGTGGTGGGAGGTGCAGCTGAGTCCCTGAGCTCCATGCCTGGCAAGAACGCAGTCACCCTGAA
GAACCGCAAAGGCTTTGTGAAGCTGGCCCTGCGCCATGGAGCTGATCTGGTTCCCACTTATTCCTTTGGA
GAGAATGAGGTATACAAGCAGGTGATCTTTGAGGAGGGTTCCTGGGGCCGATGGGTCCAGAAGAAGTTCC
AGAAGTATATTGGTTTCGCCCCCTGCATCTTCCATGGCCGAGGCCTCTTCTCCTCTGACACCTGGGGGCT
GGTGCCCTACTCCAAGCCCATCACCACCGTCGTGGGGGAGCCCATCACTGTCCCCAAGCTGGAGCACCCG
ACCCAGAAAGACATCGACCTGTACCATGCCATGTACATGGAGGCCCTGGTGAAGCTCTTTGACAATCACA
AGACCAAATTTGGCCTNCCAGAGACTGAGGTGCTGGAGGTGAACTGA (SEQ ID NO:03)

FIG. 7A

Human DAGT2α amino acid sequence

MKTLIAAYSGVLRGERQAEADRSQRSHGGPALSREGSGRWGTGSSILSALQDLFSVTWLNRSKVEKQLQV
ISVLQWVLSFLVLGVACSAILMYIFCTDCWLIAVLYFTWLVFDWNTPKKGGRRSQWVRNWAVWRYFRDYF
PIQLVKTHNLLTTRNYIFGYHPHGIMGLGAFCNFSTEATEVSKKFPGIRPYLATLAGNFRMPVLREYLMS
GGICPVSRDTIDYLLSKNGSGNAIIIVVGGAAESLSSMPGKNAVTLRNRKGFVKLALRHGADLVPIYSFG
ENEVYKQVIFEEGSWGRWVQKKFQKYIGFAPCIFHGRGLFSSDTWGLVPYSKPITTVVGEPITIPKLEHP
TQQDIDLYHTMYMEALVKLFDKHKTKFGLPETEVLEVN (SEQ ID NO:02)

FIG. 7B

Human DAGT2α nucleic acid sequence

TTCAGCCATGAAGACCCTCATAGCCGCCTACTCCGGGGTCCTGCGCGGCGAGCGTCAGGCCGAGGCTGACC
GGAGCCAGCGCTCTCACGGAGGACCCGTGTCGCGCGAGGGGTCTGGGAGATGGGGCACTGGATCCAGCATC
CTCTCCGCCCTCCAGGACCTCTTCTCTGTCACCTGGCTCAATAGGTCCAAGGTGGAAAAGCAGCTACAGGT
CATCTCAGTGCTCCAGTGGGTCCTGTCCTTCCTTGTACTGGGAGTGGCCTGCAGTGCCATCCTCATGTACA
TATTCTGCACTGATTGCTGGCTCATCGCTGTGCTCTACTTCACTTGGCTGGTGTTTGACTGGAACACACCC
AAGAAAGGTGGCAGGAGGTCACAGTGGGTCCGAAACTGGGCTGTGTGGCGCTACTTTCGAGACTACTTTCC
CATCCAGCTGGTGAAGACACACAACCTGCTGACCACCAGGAACTATATCTTTGGATACCACCCCCATGGTA
TCATGGGCCTGGGTGCCTTCTGCAACTTCAGCACAGAGGCCACAGAAGTGAGCAAGAAGTTCCCAGGCATA
CGGCCTTACCTGGCTACACTGGCAGGCAACTTCCGAATGCCTGTGTTGAGGGAGTACCTGATGTCTGGAGG
TATCTGCCCTGTCAGCCGGGACACCATAGACTATTTGCTTTCAAAGAATGGGAGTGGCAATGCTATCATCA
TCGTGGTCGGGGGTGCGGCTGAGTCTCTGAGCTCCATGCCTGGCAAGAATGCAGTCACCCTGCGGAACCGC
AAGGGCTTTGTGAAACTGGCCCTGCGTCATGGAGCTGACCTGGTTCCCATCTACTCCTTTGGAGAGAATGA
AGTGTACAAGCAGGTGATCTTCGAGGAGGGCTCCTGGGGCCGATGGGTCCAGAAGAAGTTCCAGAAATACA
TTGGTTTCGCCCCATGCATCTTCCATGGTCGAGGCCTCTTCTCCTCCGACACCTGGGGGCTGGTGCCCTAC
TCCAAGCCCATCACCACTGTTGTGGGAGAGCCCATCACCATCCCCAAGCTGGAGCACCCAACCCAGCAAGA
CATCGACCTGTACCACACCATGTACATGGAGGCCCTGGTGAAGCTCTTCGACAAGCACAAGACCAAGTTCG
GCCTCCCGGAGACTGAGGTCCTGGAGGTGAACTGAGCCAGCCTTCGGGGCCAATTCCCTGGAGGAACCAGC
TGCAAATCACTTTTTTGCTCTGTA (SEQ ID NO:01)

FIG. 8A

Mouse DC2 amino acid sequence
MMVEFAPLNTPLARCLQTAAVLQWVLSFLLLVQVCIGIMVMLVLYNYWFLYIPYLVWFYYDWRTPEQGGR
RWNWVQSWPVWKYFKEYFPICLVKTQDLDPGHNYIFGFIIPHGIFVPGAFGNFCTKYSDFKKLFPGFTSYL
HVAKIWFCFPLFREYLMSNGPVSVSKESLSHVLSKDGGGNVSIIVLGGAKEALEAHPGTFTLCIRQRKGF
VKMALTHGASLVPVFSFGENDLYKQINNPKGSWLRTIQDAMYDSMGVALPLIYARGIFQHYFGIMPYRKL
IYTVVGRPIPVQQILNPTSEQIEELHQTYLEELKKLFNEHKGKYGIPEHETLVFK (SEQ ID NO:06)

Mouse DC2 nucleic acid sequence
ATGATGGTCGAGTTCGCGCCACTCAACACCCCGCTGGCACGGTGCCTACAGACCGCTGCGGTGCTGCAGT
GGGTCCTGTCCTTCCTCCTGCTCGTGCAGGTGTGCATTGGAATTATGGTGATGCTGGTCCTGTACAACTA
TTGGTTCCTTTACATCCCATATCTGGTCTGGTTTTACTATGACTGGAGAACCCCAGAGCAAGGAGGCAGA
AGATGGAACTGGGTCCAAAGCTGGCCTGTGTGGAAGTATTTTAAGGAGTATTTTCCAATCTGTCTTGTCA
AAACGCAGGATTTGGATCCGGGTCACAATTATATATTTGGGTTTCACCCTCATGGAATATTCGTGCCTGG
AGCCTTTGGAAATTTTTGTACAAAATACTCGGACTTCAAGAAGCTATTTCCTGGCTTTACATCGTATCTC
CACGTGGCCAAGATCTGGTTCTGTTTCCCGTTGTTCCGAGAATATCTGATGAGTAACGGGCCGGTTTCAG
TGTCTAAGGAGAGTTTGTCTCATGTGCTGAGCAAGGATGGAGGTGGCAATGTCTCAATCATTGTCCTCGG
AGGTGCAAAGGAGGCGCTGGAGGCTCACCCAGGAACATTCACCCTGTGCATCCGCCAGCGCAAAGGGTTT
GTTAAGATGGCCTTGACCCATGGTGCCAGTTTGGTTCCAGTATTTTCTTTTGGTGAAAATGATCTATATA
AGCAAATTAACAACCCCAAAGGCTCCTGGCTACGAACTATACAAGACGCAATGTATGATTCAATGGGAGT
AGCCTTGCCACTGATATATGCCAGAGGAATTTTCCAGCACTACTTTGGCATAATGCCCTATCGGAAGCTG
ATCTACACTGTTGTTGGCCGCCCTATCCCTGTTCAGCAGATTCTGAACCCGACCTCAGAGCAGATTGAAG
AGCTGCATCAGACATACCTAGAGGAGCTAAAGAAACTATTCAATGAACACAAAGGGAAATATGGGATTCC
GGAGCACGAAACTCTGGTATTTAAATAA (SEQ ID NO:05)

Human DC2 amino acid sequence
MKVEFAPLNIQLARRLQTVAVLQWVLSFLTGPMSIGITVMLIIHNYLFLYIPYLMWLYFDWHTPERGGRR
SSWIKNWTLWKHFKDYFPIHLIKTQDLDPSHNYIFGFHPHGIMAVGAFGNFSVNYSDFKDLFPGFTSYLH
VLPLWFWCPVFREYVMSVGLVSVSKKSVSYMVSKEGGGNISVIVLGGAKESLDAHPGKFTLFIRQRKGFV
KIALTHGASLVPVVSFGENELFKQTDNPEGSWIRTVQNKLQKIMGFALPLFHARGVFQYNFGLMTYRKAI
HTVVGRPIPVRQTLNPTQEQIEELHQTYMEELRKLFEEHKGKYGIPEHETLVLK (SEQ ID NO:08)

Human DC2 nucleic acid sequence
CGTGGGTGCAGGCTGCAGTGGCTGGCGCCGTCCTCGCCCGGCCAGGCCATGAAGGTAGAGTTTGCACCGC
TCAACATCCAGCTGGCGCGGCGGCTGCAGACGGTGGCCGTGCTGCAGTGGGTCCTTTCTTTTCTTACAGG
GCCGATGTCCATTGGAATCACTGTGATGCTGATCATACACAACTATTTGTTCCTTTACATCCCTTATTTG
ATGTGGCTTTACTTTGACTGGCATACCCCAGAGCGAGGAGGCAGGAGATCCAGCTGGATCAAAAATTGGA
CTCTTTGGAAACACTTTAAGGACTATTTTCCAATTCATCTTATCAAAACTCAAGATTTGGATCCAAGTCA
CAACTATATATTTGGGTTTCACCCCCATGGAATAATGGCAGTTGGAGCCTTTGGGAATTTTTCTGTAAAT
TATTCTGACTTCAAGGACCTGTTTCCTGGCTTTACTTCATATCTTCACGTGCTGCCACTTTGGTTCTGGT
GTCCTGTCTTTCGAGAATATGTGATGAGTGTTGGCTGGTTTCAGTTTCCAAGAAAAGTGTGTCCTACAT
GGTAAGCAAGGAGGGAGGTGGAAACATCTCTGTCATTGTCCTTGGGGGTGCAAAAGAATCACTGGATGCT
CATCCTGGAAAGTTCACTCTGTTCATCCGCCAGCGGAAAGGATTTGTTAAAATTGCTTTGACCCATGGCG
CCTCTCTGGTCCCAGTGGTTTCTTTTGGTGAAAATGAACTGTTTAAACAAACTGACAACCCTGAAGGATC
ATGGATTAGAACTGTTCAGAATAAACTGCAGAAGATCATGGGGTTTGCTTTGCCCCTGTTTCATGCCAGG
GGAGTTTTTCAGTACAATTTTGGCCTAATGACCTATAGGAAAGCCATCCACACTGTTGTTGGCCGCCCGA
TCCCTGTTCGTCAGACTCTGAACCCGACCCAGGAGCAGATTGAGGAGTTACATCAGACCTATATGGAGGA
ACTTAGGAAATTGTTTGAGGAACACAAAGGAAAGTATGGCATTCCAGAGCACGAGACTCTTGTTTTAAAA
TGACTTGACTATAAAAAAAATTAAAAAATAAAAATAAATGACTTGGCTGTAATAAGGCATAAAGAAGGA
TAAGAGACC (SEQ ID NO:07)

FIG. 8B

Mouse DC3 amino acid sequence (partial sequence, about 100 amino acids gap in the center of the protein)

MKTEHLQSLSLLQWPLSYVAMFWIVQPLLICLLFTPLWPLPTVYFVWLLLDWKTPDKGGRRSDWVRNWNV
WNHIRDYFPITILKTKDLSPSENYIMGVHPHGLLTFGAFCNFCTEATGFSKTFPGITPHLATLSWFFKIP
IIRDYIMAKGLCSVSQASIDYLLSHGTGNLVGIPIITVVGEALPLPQVKNPSPEIVDKYHALYMDALYKL
FEQHKVQYGCSNTQKLIFL (SEQ ID NO:10)

Mouse DC3 nucleic acid sequence (partial sequence, about 100 amino acids gap in the center of the protein)

TTACCTCCCTCAGGGTCCTGGGCATCATGTCTTGCTCTATGAAGACTGAACACTTACAGAGTCTGAGCCTT
CTGCAGTGGCCCTTGAGCTACGTTGCCATGTTTTGGATTGTGCAGCCATTGTTAATTTGCCTATTGTTCAC
ACCCTTGTGGCCGCTACCAACAGTTTACTTTGTCTGGTTACTTCTCGACTGGAAGACTCCAGATAAAGGTG
GCAGGCGTTCAGACTGGGTACGGAACTGGAATGTCTGGAACCACATCAGGGACTATTTCCCCATTACAATC
CTGAAGACTAAGGACCTGTCACCTTCAGAGAACTACATCATGGGGGTCCACCCCATNGGTCTCCTGACCTT
CGGTGCCTTCTGCAACTTCTGCACTGAGGCCACAGGCTTCTCGAAGACCTTCCCAGGCATCACTCCTCACT
TGGCCACAC (SEQ ID NO:09)

Human DC3 amino acid sequence

MAFFSRLNLQEGLQTFFVLQWIPVYIFLVWILQPLFVYLLFTSLWPLPVLYFAWLFLDWKTPERGGRRSA
WVRNWCVWTHIRDYFPITILKTKDLSPEHNYLMGVHPHGLLTFGAFCNFCTEATGFSKTFPGITPHLATL
SWFFKIPFVREYLMAKGVCSVSQPAINYLLSHGTGNLVGIVVGGVGEALQSVPNTTTLILQKRKGFVRTA
LQHGAYLVPSYSFGENEVFNQETFPEGTWLRLFQKTFQDTFKKILGLNFCTFHGRGFTRGSWGFLPFNRP
ITTVVGEPLPIPRIKRPNQKTVDKYHALYISALRKLFDQHKVEYGLPETQELTIT (SEQ ID NO:12)

Human DC3 nucleic acid sequence

ATCAACTCAGCTTAAGAAGTTTTGGCCTTCTGGTTAGGCTTCTTGCCACAACAGAACAGCACCATAACCAT
GGCTTTCTTCTCCCGACTGAATCTCCAGGAGGGCCTCCAAACCTTCTTTGTTTTGCAATGGATCCCAGTCT
ATATATTTTTAGTTTGGATCTTGCAGCCATTGTTCGTCTACCTGCTGTTTACATCCTTGTGGCCGCTACCA
GTGCTTTACTTTGCCTGGTTGTTCCTGGACTGGAAGACCCCAGAGCGAGGTGGCAGGCGTTCGGCCTGGGT
AAGGAACTGGTGTGTCTGGACCCACATCAGGGACTATTTCCCCATTACGATCCTGAAGACAAAGGACCTAT
CACCTGAGCACAACTACCTCATGGGGGTTCACCCCATGGCCTCCTGACCTTTGGCGCCTTCTGCAACTTC
TGCACTGAGGCCACAGGCTTCTCGAAGACCTTCCCAGGCATCACTCCTCACTTGGCCACGCTGTCCTGGTT
CTTCAAGATCCCCTTTGTTAGGGAGTACCTCATGGCCAAAGGTGTGTGCTCTGTGAGCCAGCCAGCCATCA
ACTATCTGCTGAGCCATGGCACTGGCAACCTCGTGGGCATTGTAGTGGGAGGTGTGGGTGAGGCCCTGCAA
AGTGTGCCCAACACCACCACCCTCATCCTCCAGAAGCGCAAGGGGTTCGTGCGCACAGCCCTCCAGCATGG
GGCATACCTTGTCCCCTTCATATTCCTTTGGTGAGAACGAAGTTTTCAATCAGGAGACCTTCCCTGAGGGCA
CGTGGTTAAGGTTGTTCCAAAAAACCTTCCAGGACACATTCAAAAAAATCCTGGGACTAAATTTCTGTACC
TTCCATGGCCGGGGCTTCACTCGCGGATCCTGGGGCTTCCTGCCTTTCAATCGGCCCATTACCACTGTTGT
TGGGGAACCCCTTCCAATTCCCAGGATTAAGAGGCCAAACCAGAAGACAGTAGACAAGTATCACGCACTCT
ACATCAGTGCCCTGCGCAAGCTCTTTGACCAACACAAAGTTGAATATGGCCTCCCTGAGACCCAAGAGCTG
ACAATTACATAACAGGAGCCACATTCCCCATTGATCAACCCCCAAAGCCATGAGGGATCCAAGTAGAGCCA
CAGAAAAAGAAGAATTCCAGGAGAGGGAAAGATCGTAAGGATGAGAGAGGAGACCATCCAAGCCAGAAATT
ATTTAATAAATCAGAGTTCTAGCAATAGAGTCC (SEQ ID NO:11)

FIG. 8C

Human DC4 amino acid sequence

MLLPSKKDLKTALDVFAVFQWSFSALLITTTVIAVNLYLVVFTPYWPVTVLILTWLAFDWKTPQRGGRRF
TCVRHWRLWKHYSDYFPLKLLKTHDICPSRNYILVCHPHGLFAHGWFGHFATEASGFSKIFPGITPYILT
LGAFFWMPFLREYVMSTGACSVSRSSIDFLLTHKGTGNMVIVVIGGLAECRYSLPGSSTLVLKNRSGFVR
MALQHGVPLIPAYAFGETDLYDQHIFTPGGFVNRFQKWFQSMVHIYPCAFYGRGFTKNSWGLLPYSRPVT
TIVGEPLPMPKIENPSQEIVAKYHTLYIDALRKLFDQHKTKFGISETQELEII (SEQ ID NO:014)

Human DC4 nucleic acid sequence

AATTCGGCTTACTCACTATAGGGCTCGAGCGGCCCCCGGGCAGGTGCCGACTTCATTTCCAAGTCTGCAC
ACAATGCAGGCAGTAGCCATGCCTGACAGCCACATGACAGATACTACACCGCTGAATGTGCTCTAACCCT
GGACTTGGCATTGCCCCTACTGTTGAGGAAGCAGTGCGTTTTCTCCAGTCTTTCAGGTCCCTTCACCAG
GGAACCATTAACTTGTGCATCAGAACAAGGACATTTCCTTACATTCCTGCAAACACAGTCCTTTCAGTTT
ACTCTTTTTTTGAGGGGGGGGCGCGGGGAACGGAGTCTCGCTCTGTCGCCCAGGCTGGAGTGCAATGGTG
CAATCTCAGCTCACTGCAACCTCTGCCTCCCAGGTCCAAGCGATTCTCCTGCCTCAGCCTCCCGGGTAGC
CGGGACTACAGGCGCCTGCCACCACGCCCGGCTAATTTTTGTATTTTTAGTAGAGACGAGGTTTCGCCGT
GTTGGCAGGCTGGTCTTGGAACTCCTGACCTCAGGTGATTTACTCGCCTCGGCCTCCCAAAGTGCTGGGA
TTACAGGCATGAGCCACTGTGCCCAGTCACAAGTTTTTATTTTAGCCATTTTGATAAGTGTGAAGTTCCC
TGATGGCTAATGATGTTCCTTTTTCCATGTGCTCATTTGTCATCTATGCCAGAGAAGATTTGGAGAGGAG
GACGTGAATTGGAGGAAAACTGTTCCAGGATTCCCCACCTCTGGTGGCCCACCGCTGGCTCACTGCCATT
GACCACACTGCAGGCAGAGCCTAGTGCAGTGCTGGAGCAGGGCCCAGAGAGGAGAGGGCTTACAGTGTGA
ATTCAGCTCAGCTGGGGAAGAAGACACCTTCCCTTCTAGACCTGAATCGGGTTCCCAAGCAACCACTGTG
ATTGCTGTCAACCTCTACCTGGTGGTGTTCACACCATACTGGCCTGTCACTGTGCTTATTCTTACCTGGC
TGGCTTTTGACTGGAAGACCCCTCAGCGAGGCGGCCGCCGGTTTACCTGTGTGAGGCACTGGCGCCTGTG
GAAACACTACAGCGATTATTTCCCTCTCAAGCTTCTGAAGACTCATGACATCTGCCCCAGCCGCAACTAC
ATCCTCGTCTGCCACCCTCATGGGCTCTTTGCCCATGGATGGTTTGGCCACTTTGCCACAGAGGCCTCAG
GCTTCTCCAAGATATTTCCTGGCATCACCCCTTACATACTCACACTGGGAGCCTTTTTCTGGATGCCTTT
CCTCAGAGAATATGTAATGTCTACAGGGGCCTGCTCTGTGAGTCGATCCTCCATTGACTTTCTGCTGACT
CATAAAGGCACAGGCAACATGGTCATTGTGGTGATTGGTGGACTGGCTGAGTGCAGATACAGCCTGCCAG
GTTCTTCTACCCTGGTGTTGAAGAACCGGTCTGGCTTTGTGCGCATGGCCCTTCAGCATGGGGTGCCTCT
AATACCTGCCTATGCCTTTGGGGAGACGGACCTCTATGATCAGCACATTTTCACTCCTGGTGGCTTTGTC
AACCGCTTCCAGAAGTGGTTCCAGAGCATGGTACACATCTACCCTTGTGCTTTCTATGGACGTGGCTTCA
CCAAGAACTCCTGGGGCCTTCTGCCCTATAGTCGGCCTGTAACCACCATCGTCGGGGAGCCTCTACCAAT
GCCCAAGATTGAGAATCCAAGCCAGGAGATCGTGGCTAAATATCACACACTCTATATTGATGCCCTACGT
AAACTGTTTGACCAGCATAAGACCAAGTTTGGTATCTCAGAGACCCAGGAGCTGGAGATAATTTGACAGA
CATCCCCAGTAGCCTTCACCCTGGCTGGAAGGTATGGATGGACCCAGTGAGA (SEQ ID NO:013)

FIG. 8D

Human DC5 amino acid sequence

MVEFAPLFVPWERRLQTLAVLQFVFSFLALGKICTVGFIALLFTRFWLLTVLYAAWWYLDRDKPRQGGRH
IQAIRCWTIWKYMKDYFPIQLVKTAELDPSRNYIAGFHPHGVLAVGAFANLCTESTGFSSIFPGIRPHLM
MLTLWFRAPFFRDYIMSAGLVTSEKESAAHILNRKGGGNLLGIIVGGAQEALDARPGSFTLLLRNRKGFV
RLALTHGAPLVPIFSFGENDLFDQIPNSSGSWLRYIQNRLQKIMGISLPLFHGRGVFQYSFGLIPYRRPI
TTVGKPIEVQKTLHPSEEEVNQLHQHYIKELCNLFEAHKLKFNIPADQHLEFC (SEQ ID NO:16)

Human DC5 nucleic acid sequence

CCACAGCAGAGCTCACAGAACCTGCGGGAGCCAGGCTGACCCGCCAGCATGGTAGAGTTCGCGCCCTTGT
TTGTGCCGTGGGAGCGCAGGCTGCAGACACTTGCTGTCCTACAGTTTGTCTTCTCCTTCTTGGCACTGGG
TAAGATCTGCACTGTGGGCTTCATAGCCCTCCTGTTTACAAGATTCTGGCTCCTCACTGTCCTGTATGCG
GCCTGGTGGTATCTGGACCGAGACAAGCCACGGCAGGGGGGCCGGCACATCCAGGCCATCAGGTGCTGGA
CTATATGGAAGTACATGAAGGACTATTTCCCCATCCAGCTGGTCAAGACTGCTGAGCTGGACCCCTCTCG
GAACTACATTGCGGGCTTCCACCCCCATGGAGTCCTGGCAGTCGGAGCCTTTGCCAACCTGTGCACTGAG
AGCACAGGCTTCTCTTCGATCTTCCCCGGTATCCGCCCCCATCTGATGATGCTGACCTTGTGGTTCCGGG
CCCCCTTCTTCAGAGATTACATCATGTCTGCAGGGTTGGTCACATCAGAAAAGGAGAGTGCTGCTCACAT
TCTGAACAGGAAGGGTGGCGGAAACTTGCTGGGCATCATTGTAGGGGGTGCCCAGGAGGCCCTGGATGCC
AGGCCTGGATCCTTCACGCTGTTACTGCGGAACCGAAAGGGCTTCGTCAGGCTCGCCCTGACACACGGGG
CACCCCTGGTGCCAATCTTCTCCTTCGGGGAGAATGACCTATTTGACCAGATTCCCAACTCTTCTGGCTC
CTGGTTACGCTATATCCAGAATCGGTTGCAGAAGATCATGGGCATCTCCCTCCCACTCTTTCATGGCCGT
GGTGTCTTCCAGTACAGCTTTGGTTTAATACCCTACCGCCGGCCCATCACCACTGTGGGGAAGCCCATCG
AGGTACAGAAGACGCTGCATCCCTCGGAGGAGGAGGTGAACCAGCTGCACCAGCATTATATCAAAGAGCT
GTGCAACCTCTTCGAGGCCCACAAACTTAAGTTCAACATCCCTGCTGACCAGCACTTGGAGTTCTGCTGA
(SEQ ID NO:15)

SEQUENCE LISTING

<160> NUMBER OF SEQ ID NOS: 16

<210> SEQ ID NO 1
<211> LENGTH: 1231

<212> TYPE: DNA
<213> ORGANISM: Homo sapiens

<400> SEQUENCE: 1

```
ttcagccatg aagaccctca tagccgccta ctccggggtc ctgcgcggcg agcgtcaggc      60
cgaggctgac cggagccagc gctctcacgg aggacccgtg tcgcgcgagg ggtctgggag     120
atggggcact ggatccagca tcctctccgc cctccaggac ctcttctctg tcacctggct     180
caataggtcc aaggtggaaa agcagctaca ggtcatctca gtgctccagt gggtcctgtc     240
cttccttgta ctgggagtgg cctgcagtgc catcctcatg tacatattct gcactgattg     300
ctggctcatc gctgtgctct acttcacttg gctggtgttt gactggaaca cacccaagaa     360
aggtggcagg aggtcacagt gggtccgaaa ctgggctgtg tggcgctact tcgagacta     420
ctttcccatc cagctggtga agacacacaa cctgctgacc accaggaact atatctttgg     480
ataccacccc catggtatca tgggcctggg tgccttctgc aacttcagca cagaggccac     540
agaagtgagc aagaagttcc caggcatacg gccttacctg gctacactgg caggcaactt     600
ccgaatgcct gtgttgaggg agtacctgat gtctggaggt atctgccctg tcagccggga     660
caccatagac tatttgcttt caaagaatgg gagtggcaat gctatcatca tcgtggtcgg     720
gggtgcggct gagtctctga gctccatgcc tggcaagaat gcagtcaccc tgcggaaccg     780
caagggcttt gtgaaactgg ccctgcgtca tggagctgac ctggttccca tctactcctt     840
tggagagaat gaagtgtaca agcaggtgat cttcgaggag gctcctgggg ccgatgggt     900
ccagaagaag ttccagaaat acattggttt cgccccatgc atcttccatg gtcgaggcct     960
cttctcctcc gacacctggg gctggtgcc ctactccaag cccatcacca ctgttgtggg    1020
agagcccatc accatcccca gctggagca cccaacccag caagacatcg acctgtacca    1080
caccatgtac atggaggccc tggtgaagct cttcgacaag cacaagacca agttcggcct    1140
cccggagact gaggtcctgg aggtgaactg agccagcctt cggggccaat tccctggagg    1200
aaccagctgc aaatcacttt tttgctctgt a                                   1231
```

<210> SEQ ID NO 2
<211> LENGTH: 388
<212> TYPE: PRT
<213> ORGANISM: Homo sapiens

<400> SEQUENCE: 2

```
Met Lys Thr Leu Ile Ala Ala Tyr Ser Gly Val Leu Arg Gly Glu Arg
  1               5                  10                  15

Gln Ala Glu Ala Asp Arg Ser Gln Arg Ser His Gly Gly Pro Ala Leu
             20                  25                  30

Ser Arg Glu Gly Ser Gly Arg Trp Gly Thr Gly Ser Ser Ile Leu Ser
         35                  40                  45

Ala Leu Gln Asp Leu Phe Ser Val Thr Trp Leu Asn Arg Ser Lys Val
     50                  55                  60

Glu Lys Gln Leu Gln Val Ile Ser Val Leu Gln Trp Val Leu Ser Phe
 65                  70                  75                  80

Leu Val Leu Gly Val Ala Cys Ser Ala Ile Leu Met Tyr Ile Phe Cys
                 85                  90                  95

Thr Asp Cys Trp Leu Ile Ala Val Leu Tyr Phe Thr Trp Leu Val Phe
            100                 105                 110

Asp Trp Asn Thr Pro Lys Lys Gly Gly Arg Arg Ser Gln Trp Val Arg
        115                 120                 125
```

```
Asn Trp Ala Val Trp Arg Tyr Phe Arg Asp Tyr Phe Pro Ile Gln Leu
            130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Ser Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255

Arg Asn Arg Lys Gly Phe Val Lys Leu Ala Leu Arg His Gly Ala Asp
            260                 265                 270

Leu Val Pro Ile Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Ile Pro Lys Leu Glu His Pro Thr Gln
            340                 345                 350

Gln Asp Ile Asp Leu Tyr His Thr Met Tyr Met Glu Ala Leu Val Lys
        355                 360                 365

Leu Phe Asp Lys His Lys Thr Lys Phe Gly Leu Pro Glu Thr Glu Val
    370                 375                 380

Leu Glu Val Asn
385

<210> SEQ ID NO 3
<211> LENGTH: 1167
<212> TYPE: DNA
<213> ORGANISM: Mus musculus
<220> FEATURE:
<221> NAME/KEY: misc_feature
<222> LOCATION: 1137
<223> OTHER INFORMATION: n = A,T,C or G

<400> SEQUENCE: 3
atgaagaccc tcatcgccgc ctactccggg gtcctgcggg gtgagcgtcg ggcggaagct      60
gcccgcagcg aaaacaagaa taaggatct gccctgtcac gcgagggtc tgggcgatgg       120 ggcactggct ccagcatcct ctcagccctc aagacatct tctctgtcac ctggctcaac      180
agatcyaagg tggaaaaaca gctgcaggtc atctcagtac acaatgggt cctatccttc      240 ctggtgctag gagtggcctg cagtgtcatc ctcatgtaca ccttctgcac agactgctgg    300
ctgatagctg tgctctactt cacctggctg gcatttgact ggaacacgcc caagaaaggt   360
ggcaggagat cgcagtgggt gcgaaactgg gcgtgtggc gctacttccg agactacttt     420
cccatccagc tggtgaagac acacaacctg ctgaccacca ggaactatat ctttggatac  480
```

```
cacccccatg gcatcatggg cctgggtgcc ttctgtaact tcagcacaga ggctactgaa    540
gtcagcaaga agtttcctgg cataaggccc tatttggcta cgttggcygg taacttccgg    600
atgcctgtgc ttcgcgagta cctgatgtct ggaggcatct gccctgtcaa ccgagacacc    660
atagactact tgctctccaa gaatgggagt ggcaatgcta tcatcatcgt ggtgggaggt    720
gcagctgagt ccctgagctc catgcctggc aagaacgcag tcaccctgaa gaaccgcaaa    780
ggctttgtga agctggccct cgccatggac gctgatctgg ttcccactta ttcctttgga    840
gagaatgagg tatacaagca ggtgatcttt gaggagggtt cctggggccg atgggtccag    900
aagaagttcc agaagtatat tggtttcgcc ccctgcatct tccatggccg aggcctcttc    960
tcctctgaca cctgggggct ggtgccctac tccaagccca tcaccaccgt cgtggggag    1020 cccatcactg tccccaagct ggagcacccg acccagaaag acatcgacct gtaccatgcc    1080
atgtacatgg aggccctggt gaagctcttt gacaatcaca agaccaaatt tggcctncca    1140
gagactgagg tgctggaggt gaactga                                        1167
```

<210> SEQ ID NO 4
<211> LENGTH: 387
<212> TYPE: PRT
<213> ORGANISM: Mus musculus

<400> SEQUENCE: 4

```
Met Lys Thr Leu Ile Ala Ala Tyr Ser Gly Val Leu Arg Gly Glu Arg
 1               5                   10                  15

Arg Ala Glu Leu Pro Ala Ala Lys Asn Lys Asn Lys Gly Ser Ala Leu
            20                  25                  30

Ser Arg Glu Gly Ser Gly Arg Trp Gly Thr Gly Ser Ser Ile Leu Ser
        35                  40                  45

Ala Leu Gln Asp Ile Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Leu Val Asn Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255
```

Lys Asn Arg Lys Gly Phe Val Lys Leu Ala Leu Arg His Gly Ala Asp
         260                 265                 270

Leu Val Pro Thr Tyr Ser Phe Gly Glu Asn Glu Val Tyr Lys Gln Val
     275                 280                 285

Ile Phe Glu Glu Gly Ser Trp Gly Arg Trp Val Lys Lys Phe Gln Lys
     290                 295                 300

Tyr Ile Gly Phe Ala Pro Cys Ile Phe His Gly Arg Gly Leu Phe Ser
305                 310                 315                 320

Ser Asp Thr Trp Gly Leu Val Pro Tyr Ser Lys Pro Ile Thr Thr Val
             325                 330                 335

Val Gly Glu Pro Ile Thr Val Pro Lys Leu Glu His Pro Thr Gln Lys
         340                 345                 350

Asp Ile Asp Leu Tyr His Ala Met Tyr Met Glu Ala Leu Val Lys Leu
         355                 360                 365

Phe Asp Asn His Lys Thr Lys Phe Gly Leu Pro Glu Thr Glu Val Leu
     370                 375                 380

Glu Val Asn
385

<210> SEQ ID NO 5
<211> LENGTH: 1008
<212> TYPE: DNA
<213> ORGANISM: Mus musculus

<400> SEQUENCE: 5
atgatggtcg agttcgcgcc actcaacacc ccgctggcac ggtgcctaca gaccgctgcg      60
gtgctgcagt gggtcctgtc cttcctcctg ctcgtgcagg tgtgcattgg aattatggtg     120
atgctggtcc tgtacaacta ttggttcctt acatcccat atctggtctg gttttactat     180
gactggagaa ccccagagca aggaggcaga agatggaact gggtccaaag ctggcctgtg     240
tggaagtatt ttaaggagta ttttccaatc tgtcttgtca aaacgcagga tttggatccg     300
ggtcacaatt atatatttgg gttcaccct catggaatat cgtgcctgg agcctttgga     360
aattttgta caaaatactc ggacttcaag aagctatttc ctggctttac atcgtatctc     420
cacgtggcca agatctggtt ctgtttcccg ttgttccgag aatatctgat gagtaacggg     480
ccggtttcag tgtctaagga gagtttgtct catgtgctga gcaaggatgg aggtggcaat     540
gtctcaatca ttgtcctcgg aggtgcaaag gaggcgctgg aggctcaccc aggaacattc     600
accctgtgca tccgccagcg caaagggttt gttaagatgg ccttgaccca tggtgccagt     660
ttggttccag tattttcttt tggtgaaaat gatctatata agcaaattaa caaccccaaa     720
ggctcctggc tacgaactat acaagacgca atgtatgatt caatgggagt agccttgcca     780
ctgatatatg ccagaggaat tttccagcac tactttggca taatgcccta tcggaagctg     840
atctacactg ttgttggccg ccctatccct gttcagcaga ttctgaaccc gacctcagag     900
cagattgaag agctgcatca gacataccta gaggagctaa agaaactatt caatgaacac     960
aaagggaaat atgggattcc ggagcacgaa actctggtat ttaaataa              1008

<210> SEQ ID NO 6
<211> LENGTH: 335
<212> TYPE: PRT
<213> ORGANISM: Mus musculus

<400> SEQUENCE: 6

Met Met Val Glu Phe Ala Pro Leu Asn Thr Pro Leu Ala Arg Cys Leu

```
  1               5                  10                  15
Gln Thr Ala Ala Val Leu Gln Trp Val Leu Ser Phe Leu Leu Leu Val
                 20                  25                  30

Gln Val Cys Ile Gly Ile Met Val Met Leu Val Leu Tyr Asn Tyr Trp
                 35                  40                  45

Phe Leu Tyr Ile Pro Tyr Leu Val Trp Phe Tyr Tyr Asp Trp Arg Thr
                 50                  55                  60

Pro Glu Gln Gly Gly Arg Arg Trp Asn Trp Val Gln Ser Trp Pro Val
 65                  70                  75                  80

Trp Lys Tyr Phe Lys Glu Tyr Phe Pro Ile Cys Leu Val Lys Thr Gln
                 85                  90                  95

Asp Leu Asp Pro Gly His Asn Tyr Ile Phe Gly Phe His Pro His Gly
                100                 105                 110

Ile Phe Val Pro Gly Ala Phe Gly Asn Phe Cys Thr Lys Tyr Ser Asp
                115                 120                 125

Phe Lys Lys Leu Phe Pro Gly Phe Thr Ser Tyr Leu His Val Ala Lys
                130                 135                 140

Ile Trp Phe Cys Phe Pro Leu Phe Arg Glu Tyr Leu Met Ser Asn Gly
145                 150                 155                 160

Pro Val Ser Val Ser Lys Glu Ser Leu Ser His Val Leu Ser Lys Asp
                165                 170                 175

Gly Gly Gly Asn Val Ser Ile Ile Val Leu Gly Gly Ala Lys Glu Ala
                180                 185                 190

Leu Glu Ala His Pro Gly Thr Phe Thr Leu Cys Ile Arg Gln Arg Lys
                195                 200                 205

Gly Phe Val Lys Met Ala Leu Thr His Gly Ala Ser Leu Val Pro Val
                210                 215                 220

Phe Ser Phe Gly Glu Asn Asp Leu Tyr Lys Gln Ile Asn Asn Pro Lys
225                 230                 235                 240

Gly Ser Trp Leu Arg Thr Ile Gln Asp Ala Met Tyr Asp Ser Met Gly
                245                 250                 255

Val Ala Leu Pro Leu Ile Tyr Ala Arg Gly Ile Phe Gln His Tyr Phe
                260                 265                 270

Gly Ile Met Pro Tyr Arg Lys Leu Ile Tyr Thr Val Val Gly Arg Pro
                275                 280                 285

Ile Pro Val Gln Gln Ile Leu Asn Pro Thr Ser Glu Gln Ile Glu Glu
                290                 295                 300

Leu His Gln Thr Tyr Leu Glu Glu Leu Lys Lys Leu Phe Asn Glu His
305                 310                 315                 320

Lys Gly Lys Tyr Gly Ile Pro Glu His Glu Thr Leu Val Phe Lys
                325                 330                 335

<210> SEQ ID NO 7
<211> LENGTH: 1129
<212> TYPE: DNA
<213> ORGANISM: Homo sapiens

<400> SEQUENCE: 7
cgtgggtgca ggctgcagtg gctggcgccg tcctcgcccg gccaggccat gaaggtagag      60
tttgcaccgc tcaacatcca gctggcgcgg cggctgcaga cggtggccgt gctgcagtgg     120
gtcctttctt ttcttacagg gccgatgtcc attggaatca ctgtgatgct gatcatacac     180
aactatttgt tcctttacat cccttatttg atgtggcttt actttgactg catacccca     240 gagcgaggag gcaggagatc cagctggatc aaaaaattgga ctctttggaa acactttaag   300
```

```
gactattttc caattcatct tatcaaaact caagatttgg atccaagtca caactatata    360
tttgggtttc accccatgg aataatggca gttggagcct tgggaatttt ttctgtaaat    420
tattctgact tcaaggacct gtttcctggc tttacttcat atcttcacgt gctgccactt    480
tggttctggt gtcctgtctt tcgagaatat gtgatgagtg ttgggctggt ttcagtttcc    540
aagaaaagtg tgtcctacat ggtaagcaag gagggaggtg gaaacatctc tgtcattgtc    600
cttggggtg caaaagaatc actggatgct catcctggaa agttcactct gttcatccgc    660
cagcggaaag gatttgttaa aattgctttg acccatggcg cctctctggt cccagtggtt    720
tcttttggtg aaaatgaact gtttaaacaa actgacaacc ctgaaggatc atggattaga    780
actgttcaga ataaactgca gaagatcatg gggtttgctt tgcccctgtt tcatgccagg    840
ggagttttc agtacaattt tggcctaatg acctatagga aagccatcca cactgttgtt    900
ggccgcccga tccctgttcg tcagactctg aacccgaccc aggagcagat tgaggagtta    960
catcagacct atatggagga acttaggaaa ttgtttgagg aacacaaagg aaagtatggc   1020
attccagagc acgagactct tgttttaaaa tgacttgact ataaaaaaaa attaaaaaat   1080
aaaaataaat gacttggctg taataaggca taaagaagga taagagacc              1129
```

<210> SEQ ID NO 8
<211> LENGTH: 334
<212> TYPE: PRT
<213> ORGANISM: Homo sapiens

<400> SEQUENCE: 8

```
Met Lys Val Glu Phe Ala Pro Leu Asn Ile Gln Leu Ala Arg Arg Leu
 1               5                  10                  15

Gln Thr Val Ala Val Leu Gln Trp Val Leu Ser Phe Leu Thr Gly Pro
            20                  25                  30

Met Ser Ile Gly Ile Thr Val Met Leu Ile Ile His Asn Tyr Leu Phe
        35                  40                  45

Leu Tyr Ile Pro Tyr Leu Met Trp Leu Tyr Phe Asp Trp His Thr Pro
    50                  55                  60

Glu Arg Gly Gly Arg Arg Ser Ser Trp Ile Lys Asn Trp Thr Leu Trp
65                  70                  75                  80

Lys His Phe Lys Asp Tyr Phe Pro Ile His Leu Ile Lys Thr Gln Asp
                85                  90                  95

Leu Asp Pro Ser His Asn Tyr Ile Phe Gly Phe His Pro His Gly Ile
            100                 105                 110

Met Ala Val Gly Ala Phe Gly Asn Phe Ser Val Asn Tyr Ser Asp Phe
        115                 120                 125

Lys Asp Leu Phe Pro Gly Phe Thr Ser Tyr Leu His Val Leu Pro Leu
    130                 135                 140

Trp Phe Trp Cys Pro Val Phe Arg Glu Tyr Val Met Ser Val Gly Leu
145                 150                 155                 160

Val Ser Val Ser Lys Lys Ser Val Ser Tyr Met Val Ser Lys Glu Gly
                165                 170                 175

Gly Gly Asn Ile Ser Val Ile Val Leu Gly Gly Ala Lys Glu Ser Leu
            180                 185                 190

Asp Ala His Pro Gly Lys Phe Thr Leu Phe Ile Arg Gln Arg Lys Gly
        195                 200                 205

Phe Val Lys Ile Ala Leu Thr His Gly Ala Ser Leu Val Pro Val Val
    210                 215                 220
```

```
Ser Phe Gly Glu Asn Glu Leu Phe Lys Gln Thr Asp Asn Pro Glu Gly
225                 230                 235                 240

Ser Trp Ile Arg Thr Val Gln Asn Lys Leu Gln Lys Ile Met Gly Phe
            245                 250                 255

Ala Leu Pro Leu Phe His Ala Arg Gly Val Phe Gln Tyr Asn Phe Gly
        260                 265                 270

Leu Met Thr Tyr Arg Lys Ala Ile His Thr Val Val Gly Arg Pro Ile
    275                 280                 285

Pro Val Arg Gln Thr Leu Asn Pro Thr Gln Glu Gln Ile Glu Glu Leu
290                 295                 300

His Gln Thr Tyr Met Glu Glu Leu Arg Lys Leu Phe Glu Glu His Lys
305                 310                 315                 320

Gly Lys Tyr Gly Ile Pro Glu His Glu Thr Leu Val Leu Lys
                325                 330
```

<210> SEQ ID NO 9
<211> LENGTH: 435
<212> TYPE: DNA
<213> ORGANISM: Mus musculus
<220> FEATURE:
<221> NAME/KEY: misc_feature
<222> LOCATION: 341
<223> OTHER INFORMATION: n = A,T,C or G

<400> SEQUENCE: 9

```
ttacctccct cagggtcctg ggcatcatgt cttgctctat gaagactgaa cacttacaga    60
gtctgagcct tctgcagtgg cccttgagct acgttgccat gttttggatt gtgcagccat   120
tgttaatttg cctattgttc acaccttgt ggccgctacc aacagtttac tttgtctggt    180
tacttctcga ctggaagact ccagataaag gtggcaggcg ttcagactgg gtacggaact   240
ggaatgtctg gaaccacatc agggactatt tccccattac aatcctgaag actaaggacc   300
tgtcaccttc agagaactac atcatggggg tccacccccn ggtctcctg accttcggtg    360
ccttctgcaa cttctgcact gaggccacag gcttctcgaa gaccttccca ggcatcactc   420
ctcacttggc cacac                                                    435
```

<210> SEQ ID NO 10
<211> LENGTH: 229
<212> TYPE: PRT
<213> ORGANISM: Mus musculus

<400> SEQUENCE: 10

```
Met Lys Thr Glu His Leu Gln Ser Leu Ser Leu Leu Gln Trp Pro Leu
1               5                   10                  15

Ser Tyr Val Ala Met Phe Trp Ile Val Gln Pro Leu Leu Ile Cys Leu
            20                  25                  30

Leu Phe Thr Pro Leu Trp Pro Leu Pro Thr Val Tyr Phe Val Trp Leu
        35                  40                  45

Leu Leu Asp Trp Lys Thr Pro Asp Lys Gly Gly Arg Arg Ser Asp Trp
    50                  55                  60

Val Arg Asn Trp Asn Val Trp Asn His Ile Arg Asp Tyr Phe Pro Ile
65                  70                  75                  80

Thr Ile Leu Lys Thr Lys Asp Leu Ser Pro Ser Glu Asn Tyr Ile Met
                85                  90                  95

Gly Val His Pro His Gly Leu Leu Thr Phe Gly Ala Phe Cys Asn Phe
            100                 105                 110

Cys Thr Glu Ala Thr Gly Phe Ser Lys Thr Phe Pro Gly Ile Thr Pro
```

```
              115                 120                 125
His Leu Ala Thr Leu Ser Trp Phe Phe Lys Ile Pro Ile Ile Arg Asp
    130                 135                 140

Tyr Ile Met Ala Lys Gly Leu Cys Ser Val Ser Gln Ala Ser Ile Asp
145                 150                 155                 160

Tyr Leu Ser His Gly Thr Gly Asn Leu Val Gly Ile Pro Ile Ile
                165                 170                 175

Thr Val Val Gly Glu Ala Leu Pro Leu Pro Gln Val Lys Asn Pro Ser
                180                 185                 190

Pro Glu Ile Val Asp Lys Tyr His Ala Leu Tyr Met Asp Ala Leu Tyr
                195                 200                 205

Lys Leu Phe Glu Gln His Lys Val Gln Tyr Gly Cys Ser Asn Thr Gln
    210                 215                 220

Lys Leu Ile Phe Leu
225

<210> SEQ ID NO 11
<211> LENGTH: 1240
<212> TYPE: DNA
<213> ORGANISM: Homo sapiens

<400> SEQUENCE: 11
atcaactcag cttaagaagt tttggccttc tggttaggct tcttgccaca acagaacagc      60
accataacca tggctttctt ctcccgactg aatctccagg agggcctcca aaccttcttt     120
gttttgcaat ggatcccagt ctatatattt ttagtttgga tcttgcagcc attgttcgtc     180
tacctgctgt ttacatcctt gtggccgcta ccagtgcttt actttgcctg gttgttcctg     240
gactggaaga ccccagagcg aggtggcagg cgttcggcct gggtaaggaa ctggtgtgtc     300
tggacccaca tcagggacta tttccccatt acgatcctga agacaaagga cctatcacct     360
gagcacaact acctcatggg ggttcacccc catggcctcc tgacctttgg cgccttctgc     420
aacttctgca ctgaggccac aggcttctcg aagaccttcc caggcatcac tcctcacttg     480
gccacgctgt cctggttctt caagatcccc tttgttaggg agtacctcat ggccaaaggt     540
gtgtgctctg tgagccagcc agccatcaac tatctgctga gccatggcac tggcaacctc     600
gtgggcattg tagtgggagg tgtgggtgag gccctgcaaa gtgtgcccaa caccaccacc     660
ctcatcctcc agaagcgcaa ggggttcgtg cgcacagccc tccagcatgg gcataccctt     720
gtcccttcat attcctttgg tgagaacgaa gttttcaatc aggagacctt ccctgagggc     780
acgtggttaa ggttgttcca aaaaaccttc caggacacat tcaaaaaaat cctgggacta     840
aatttctgta ccttccatgg ccggggcttc actcgcggat cctggggctt cctgcctttc     900
aatcggccca ttaccactgt tgttggggaa ccccttccaa ttcccaggat taagaggcca     960
aaccagaaga cagtagacaa gtatcacgca ctctacatca gtgccctgcg caagctcttt    1020
gaccaacaca agttgaata tggcctccct gagacccaag agctgacaat tacataacag    1080
gagccacatt ccccattgat caaccccaa agccatgagg gatccaagta gagccacaga    1140 aaagaagaa ttccaggaga gggaaagatc gtaaggatga gagaggagac catccaagcc    1200
agaaattatt taataaatca gagttctagc aatagagtcc                         1240

<210> SEQ ID NO 12
<211> LENGTH: 335
<212> TYPE: PRT
<213> ORGANISM: Homo sapiens
```

<400> SEQUENCE: 12

```
Met Ala Phe Phe Ser Arg Leu Asn Leu Gln Glu Gly Leu Gln Thr Phe
1               5                   10                  15

Phe Val Leu Gln Trp Ile Pro Val Tyr Ile Phe Leu Val Trp Ile Leu
            20                  25                  30

Gln Pro Leu Phe Val Tyr Leu Leu Phe Thr Ser Leu Trp Pro Leu Pro
            35                  40                  45

Val Leu Tyr Phe Ala Trp Leu Phe Leu Asp Trp Lys Thr Pro Glu Arg
 50                  55                  60

Gly Gly Arg Arg Ser Ala Trp Val Arg Asn Trp Cys Val Trp Thr His
65                  70                  75                  80

Ile Arg Asp Tyr Phe Pro Ile Thr Ile Leu Lys Thr Lys Asp Leu Ser
                85                  90                  95

Pro Glu His Asn Tyr Leu Met Gly Val His Pro His Gly Leu Leu Thr
            100                 105                 110

Phe Gly Ala Phe Cys Asn Phe Cys Thr Glu Ala Thr Gly Phe Ser Lys
            115                 120                 125

Thr Phe Pro Gly Ile Thr Pro His Leu Ala Thr Leu Ser Trp Phe Phe
130                 135                 140

Lys Ile Pro Phe Val Arg Glu Tyr Leu Met Ala Lys Gly Val Cys Ser
145                 150                 155                 160

Val Ser Gln Pro Ala Ile Asn Tyr Leu Leu Ser His Gly Thr Gly Asn
                165                 170                 175

Leu Val Gly Ile Val Val Gly Gly Val Gly Glu Ala Leu Gln Ser Val
            180                 185                 190

Pro Asn Thr Thr Thr Leu Ile Leu Gln Lys Arg Lys Gly Phe Val Arg
            195                 200                 205

Thr Ala Leu Gln His Gly Ala Tyr Leu Val Pro Ser Tyr Ser Phe Gly
210                 215                 220

Glu Asn Glu Val Phe Asn Gln Glu Thr Phe Pro Glu Gly Thr Trp Leu
225                 230                 235                 240

Arg Leu Phe Gln Lys Thr Phe Gln Asp Thr Phe Lys Lys Ile Leu Gly
                245                 250                 255

Leu Asn Phe Cys Thr Phe His Gly Arg Gly Phe Gly Thr Arg Gly Ser Trp
            260                 265                 270

Gly Phe Leu Pro Phe Asn Arg Pro Ile Thr Thr Val Val Gly Glu Pro
            275                 280                 285

Leu Pro Ile Pro Arg Ile Lys Arg Pro Asn Gln Lys Thr Val Asp Lys
290                 295                 300

Tyr His Ala Leu Tyr Ile Ser Ala Leu Arg Lys Leu Phe Asp Gln His
305                 310                 315                 320

Lys Val Glu Tyr Gly Leu Pro Glu Thr Gln Glu Leu Thr Ile Thr
                325                 330                 335
```

<210> SEQ ID NO 13
<211> LENGTH: 1872
<212> TYPE: DNA
<213> ORGANISM: Homo sapiens

<400> SEQUENCE: 13

```
aattcggctt actcactata gggctcgagc ggcccccggg caggtgccga cttcatttcc      60
aagtctgcac acaatgcagg cagtagccat gcctgacagc cacatgacag atactacacc     120
gctgaatgtg ctctaaccct ggacttggca ttgccctac tgttgaggaa gcagtgcgtt     180
```

-continued

```
tttctccagt ctttcaggtc ccttcaccag ggaaccatta acttgtgcat cagaacaagg      240
acatttcctt acattcctgc aaacacagtc ctttcagttt actctttttt tgagggggg       300 gcgcggggaa cggagtctcg ctctgtcgcc caggctggag tgcaatggtg caatctcagc      360
tcactgcaac ctctgcctcc caggtccaag cgattctcct gcctcagcct cccgggtagc      420
cgggactaca ggcgcctgcc accacgcccg gctaattttt gtattttag tagagacgag       480 gtttcgccgt gttggcaggc tggtcttgga actcctgacc tcaggtgatt tactcgcctc      540
ggcctcccaa agtgctggga ttacaggcat gagccactgt gcccagtcac aagtttttat      600
tttagccatt ttgataagtg tgaagttccc tgatggctaa tgatgttcct ttttccatgt      660
gctcatttgt catctatgcc agagaagatt tggagaggag gacgtgaatt ggaggaaaac      720
tgttccagga ttccccacct ctggtggccc accgctggct cactgccatt gaccacactg      780
caggcagagc ctagtgcagt gctggagcag ggcccagaga ggagagggct tacagtgtga      840
attcagctca gctggggaag aagacacctt cccttctaga cctgaatcgg gttcccaagc      900
aaccactgtg attgctgtca acctctacct ggtggtgttc accatact ggcctgtcac        960 tgtgcttatt cttacctggc tggcttttga ctggaagacc cctcagcgag gcggccgccg     1020
gtttacctgt gtgaggcact ggcgcctgtg gaaacactac agcgattatt tccctctcaa     1080
gcttctgaag actcatgaca tctgccccag ccgcaactac atcctcgtct gccaccctca     1140
tgggctcttt gcccatggat ggtttggcca ctttgccaca gaggcctcag gcttctccaa     1200
gatatttcct ggcatcaccc cttacatact cacactggga gccttttct ggatgccttt      1260 cctcagagaa tatgtaatgt ctacaggggc ctgctctgtg agtcgatcct ccattgactt     1320
tctgctgact cataaaggca caggcaacat ggtcattgtg gtgattggtg gactggctga     1380
gtgcagatac agcctgccag gttcttctac cctggtgttg aagaaccggt ctggctttgt     1440
gcgcatggcc cttcagcatg gggtgcctct aatacctgcc tatgcctttg gggagacgga     1500
cctctatgat cagcacattt tcactcctgg tggctttgtc aaccgcttcc agaagtggtt     1560
ccagagcatg gtacacatct acccttgtgc tttctatgga cgtggcttca ccaagaactc     1620
ctggggcctt ctgccctata gtcggcctgt aaccaccatc gtcggggagc ctctaccaat     1680
gcccaagatt gagaatccaa gcaggagat cgtggctaaa tatcacacac tctatattga     1740
tgccctacgt aaactgtttg accagcataa gaccaagttt ggtatctcag agacccagga     1800
gctggagata atttgacaga catccccagt agccttcacc ctggctggaa ggtatggatg     1860
gacccagtga ga                                                          1872
```

<210> SEQ ID NO 14
<211> LENGTH: 333
<212> TYPE: PRT
<213> ORGANISM: Homo sapiens

<400> SEQUENCE: 14

Met Leu Leu Pro Ser Lys Lys Asp Leu Lys Thr Ala Leu Asp Val Phe
1               5                   10                  15

Ala Val Phe Gln Trp Ser Phe Ser Ala Leu Leu Ile Thr Thr Thr Val
            20                  25                  30

Ile Ala Val Asn Leu Tyr Leu Val Val Phe Thr Pro Tyr Trp Pro Val
        35                  40                  45

Thr Val Leu Ile Leu Thr Trp Leu Ala Phe Asp Trp Lys Thr Pro Gln
    50                  55                  60

Arg Gly Gly Arg Arg Phe Thr Cys Val Arg His Trp Arg Leu Trp Lys

-continued

```
                65                  70                  75                  80
            His Tyr Ser Asp Tyr Phe Pro Leu Lys Leu Leu Lys Thr His Asp Ile
                            85                  90                  95
            Cys Pro Ser Arg Asn Tyr Ile Leu Val Cys His Pro His Gly Leu Phe
                        100                 105                 110
            Ala His Gly Trp Phe Gly His Phe Ala Thr Glu Ala Ser Gly Phe Ser
                        115                 120                 125
            Lys Ile Phe Pro Gly Ile Thr Pro Tyr Ile Leu Thr Leu Gly Ala Phe
                        130                 135                 140
            Phe Trp Met Pro Phe Leu Arg Glu Tyr Val Met Ser Thr Gly Ala Cys
            145                 150                 155                 160
            Ser Val Ser Arg Ser Ser Ile Asp Phe Leu Leu Thr His Lys Gly Thr
                            165                 170                 175
            Gly Asn Met Val Ile Val Ile Gly Gly Leu Ala Glu Cys Arg Tyr
                        180                 185                 190
            Ser Leu Pro Gly Ser Ser Thr Leu Val Leu Lys Asn Arg Ser Gly Phe
                        195                 200                 205
            Val Arg Met Ala Leu Gln His Gly Val Pro Leu Ile Pro Ala Tyr Ala
                        210                 215                 220
            Phe Gly Glu Thr Asp Leu Tyr Asp Gln His Ile Phe Thr Pro Gly Gly
            225                 230                 235                 240
            Phe Val Asn Arg Phe Gln Lys Trp Phe Gln Ser Met Val His Ile Tyr
                            245                 250                 255
            Pro Cys Ala Phe Tyr Gly Arg Gly Phe Thr Lys Asn Ser Trp Gly Leu
                        260                 265                 270
            Leu Pro Tyr Ser Arg Pro Val Thr Thr Ile Val Gly Glu Pro Leu Pro
                        275                 280                 285
            Met Pro Lys Ile Glu Asn Pro Ser Gln Glu Ile Val Ala Lys Tyr His
                        290                 295                 300
            Thr Leu Tyr Ile Asp Ala Leu Arg Lys Leu Phe Asp Gln His Lys Thr
            305                 310                 315                 320
            Lys Phe Gly Ile Ser Glu Thr Gln Glu Leu Glu Ile Ile
                            325                 330

<210> SEQ ID NO 15
<211> LENGTH: 1050
<212> TYPE: DNA
<213> ORGANISM: Homo sapiens

<400> SEQUENCE: 15
ccacagcaga gctcacagaa cctgcgggag ccaggctgac ccgccagcat ggtagagttc      60
gcgcccttgt ttgtgccgtg ggagcgcagg ctgcagacac ttgctgtcct acagtttgtc     120
ttctccttct tggcactggg taagatctgc actgtgggct tcatagcccc cctgtttaca     180
agattctggc tcctcactgt cctgtatgcg gcctggtggt atctggaccg agacaagcca     240
cggcagggggg gccggcacat ccaggccatc aggtgctgga ctatatggaa gtacatgaag     300
gactatttcc ccatccagct ggtcaagact gctgagctgg accccctctcg aactacatt     360
gcgggcttcc accccatgg agtcctggca gtcggagcct tgccaacct gtgcactgag     420
agcacaggct tctcttcgat cttccccggt atccgccccc atctgatgat gctgaccttg     480
tggttccggg cccccttctt cagagattac atcatgtctg cagggttggt cacatcagaa     540
aaggagagtg ctgctcacat tctgaacagg aaggtggcg gaaacttgct ggcatcatt     600
gtagggggtg cccaggaggc cctggatgcc aggcctggat ccttcacgct gttactgcgg     660
```

```
aaccgaaagg gcttcgtcag gctcgccctg acacacgggg cacccctggt gccaatcttc      720
tccttcgggg agaatgacct atttgaccag attcccaact cttctggctc ctggttacgc      780
tatatccaga atcggttgca gaagatcatg ggcatctccc tcccactctt tcatggccgt      840
ggtgtcttcc agtacagctt tggtttaata ccctaccgcc ggcccatcac cactgtgggg      900
aagcccatcg aggtacagaa gacgctgcat ccctcggagg aggaggtgaa ccagctgcac      960
cagcattata tcaaagagct gtgcaacctc ttcgaggccc acaaacttaa gttcaacatc     1020
cctgctgacc agcacttgga gttctgctga                                       1050

<210> SEQ ID NO 16
<211> LENGTH: 333
<212> TYPE: PRT
<213> ORGANISM: Homo sapiens

<400> SEQUENCE: 16

Met Val Glu Phe Ala Pro Leu Phe Val Pro Trp Glu Arg Arg Leu Gln
 1               5                  10                  15

Thr Leu Ala Val Leu Gln Phe Val Phe Ser Phe Leu Ala Leu Gly Lys
            20                  25                  30

Ile Cys Thr Val Gly Phe Ile Ala Leu Leu Phe Thr Arg Phe Trp Leu
        35                  40                  45

Leu Thr Val Leu Tyr Ala Ala Trp Trp Tyr Leu Asp Arg Asp Lys Pro
    50                  55                  60

Arg Gln Gly Gly Arg His Ile Gln Ala Ile Arg Cys Trp Thr Ile Trp
65                  70                  75                  80

Lys Tyr Met Lys Asp Tyr Phe Pro Ile Gln Leu Val Lys Thr Ala Glu
                85                  90                  95

Leu Asp Pro Ser Arg Asn Tyr Ile Ala Gly Phe His Pro His Gly Val
            100                 105                 110

Leu Ala Val Gly Ala Phe Ala Asn Leu Cys Thr Glu Ser Thr Gly Phe
        115                 120                 125

Ser Ser Ile Phe Pro Gly Ile Arg Pro His Leu Met Met Leu Thr Leu
    130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Arg Asn Arg Lys Gly
        195                 200                 205

Phe Val Arg Leu Ala Leu Thr His Gly Ala Pro Leu Val Pro Ile Phe
    210                 215                 220

Ser Phe Gly Glu Asn Asp Leu Phe Asp Gln Ile Pro Asn Ser Ser Gly
225                 230                 235                 240

Ser Trp Leu Arg Tyr Ile Gln Asn Arg Leu Gln Lys Ile Met Gly Ile
                245                 250                 255

Ser Leu Pro Leu Phe His Gly Arg Gly Val Phe Gln Tyr Ser Phe Gly
            260                 265                 270

Leu Ile Pro Tyr Arg Arg Pro Ile Thr Thr Val Gly Lys Pro Ile Glu
        275                 280                 285

Val Gln Lys Thr Leu His Pro Ser Glu Glu Glu Val Asn Gln Leu His
    290                 295                 300
```

```
-continued

Gln His Tyr Ile Lys Glu Leu Cys Asn Leu Phe Glu Ala His Lys Leu
305                 310                 315                 320

Lys Phe Asn Ile Pro Ala Asp Gln His Leu Glu Phe Cys
                325                 330
```

DIACYLGLYCEROL O-ACYLTRANSFERASE 2α (DGAT2α)

CROSS-REFERENCE TO RELATED APPLICATIONS

This application is a divisional application of U.S. patent application Ser. No. 09/794,715, filed Feb. 26, 2001 now abandoned, which claims benefit of priority to U.S. Provisional Patent Application No. 60/271,307, filed Feb. 23, 2001, which applications are incorporated by reference herein in their entirety.

STATEMENT REGARDING FEDERALLY SPONSORED RESEARCH

The U.S. government may have certain rights in this invention, pursuant to grant no. DK56084 awarded by the National Institutes of Health.

INTRODUCTION

1. Field of the Invention

The field of the invention is enzymes, particularly acyltransferases.

2. Background of the Invention

Diacylglycerol O-Acyltransferase (EC 2.3.1.20), also known as diglyceride acyltransferase or DGAT, is a critical enzyme in triacylglycerol synthesis. Triacylglycerols are quantitatively the most important storage form of energy for eukaryotic cells. DGAT catalyzes the rate-limiting and terminal step in triacylglycerol synthesis using diacylglycerol and fatty acyl CoA as substrates. As such, DGAT plays a fundamental role in the metabolism of cellular diacylglycerol and is important in higher eukaryotes for intestinal fat absorption, lipoprotein assembly, fat storage in adipocytes, milk production and possibly egg production and sperm maturation.

Because of its central role in a variety of different processes, there is much interest in the identification of polynucleotides encoding proteins having DGAT activity, as well as the proteins encoded thereby.

Relevant Literature

Of particular interest are: U.S. Pat. No. 6,100,077; and PCT Published Application Nos. WO 98/55631; WO 99/67268; WO 00/01713; WO 99/67403; WO 00/32793; WO 00/32756; WO 00/36114; WO 00/60095; WO 00/66749.

Also of interest are: Smith et al., Nat. Genet. 2000 (25), 87-90). Cases et al. "Identification of a gene encoding an acyl CoA:diacylglycerol acyltransferase, a key enzyme in triacylglycerol synthesis," Proc. Natl. Acad. Sci. USA (October 1998) 95:13018-13023; and Oelkers et al., "Characterization of Two Human Genes Encoding Acyl Coenzyme A: Cholesterol Acyltransferase-Related Enzymes," J. Biol. Chem. (Oct. 9, 1998) 273:26765-71.

References describing the role DGAT plays in various biological processes include: Bell & Coleman, "Enzymes of Glycerolipid Synthesis in Eukaryotes," Annu. Rev. Biochem. (1980) 49: 459-487; Lehner & Kuksis, "Biosynthesis of Triacylglycerols," Prog. Lipid Res. (1996) 35: 169-201; Brindley, Biochemistry of Lipids, Lipoproteins and Membranes (eds. Vance & Vance)(Elsevier, Amsterdam)(1991) pp 171-203; Haagsman & Van Golde, "Synthesis and Secretion of Very Low Density Lipoproteins by Isolated Rat Hepatocytes in Suspension: Role of Diacylglycerol Acyltransferase," Arch. Biochem. Biophys. (1981) 208:395-402; Coleman & Bell, "Triacylglycerol Synthesis in Isolated Fat Cells. Studies on the Microsomal Diacylglycerol Acyltransferase Activity Using Ethanol-Dispersed Diacylglycerols," J. Biol. Chem. (1976) 251:4537-4543.

SUMMARY OF THE INVENTION

Nucleic acid compositions encoding polypeptide products with diglyceride acyltransferase activity, as well as the polypeptide products encoded thereby, i.e., mammalian DGAT2α polypeptide products, and methods for producing the same, are provided. Also provided are: methods and compositions for modulating DGAT2α activity; DGAT2α transgenic cells, animals and plants, as well as methods for their preparation; and methods for making triglycerides and triglyceride compositions, as well as the compositions produced by these methods. The subject methods and compositions find use in a variety of different applications, including research, medicine, agriculture and industry applications.

BRIEF DESCRIPTION OF THE FIGURES

FIG. 2 provides a hydrophobicity plot of mouse DGAT2α.

FIGS. 3A to 3C provide graphical results of various mouse DGAT2α activity assays.

FIG. 4 provides the expression profile for mouse DGAT2α.

FIGS. 6A and 6B provide the amino acid and nucleic acid sequences of mouse DGAT2α.

FIGS. 7A and 7B provide the amino acid and nucleic acid sequences of human DGAT2α.

FIG. 8 provides the amino acid and nucleic acid sequences of various mouse and human DGAT2α homologs.

DETAILED DESCRIPTION OF THE INVENTION

Figure 1:
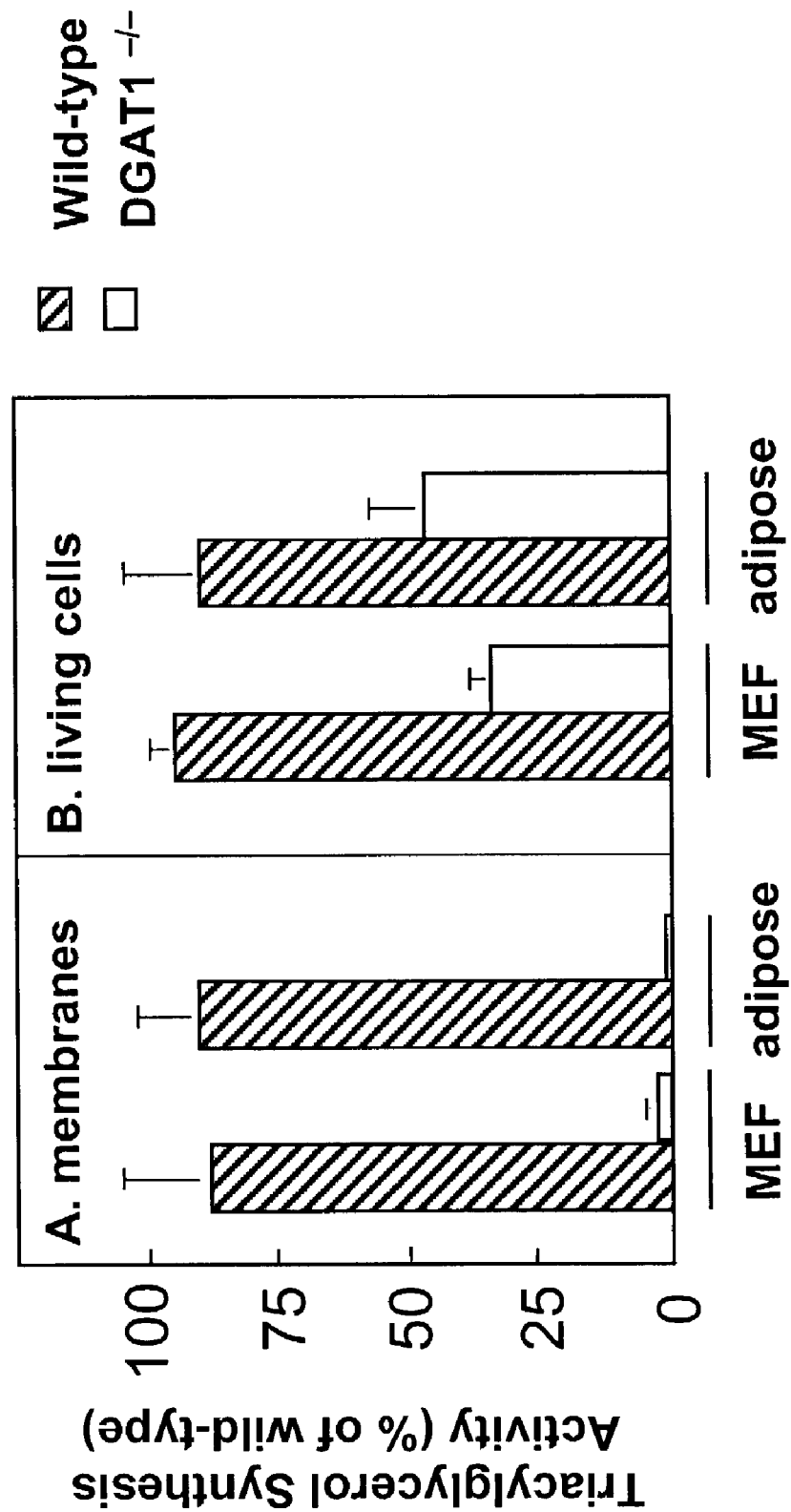
FIG. 1 provides a graphical representation of the results obtained from a pulse assay that demonstrates the existence of mouse DGAT2α.

Nucleic acid compositions encoding polypeptide products with diglyceride acyltransferase activity, as well as the polypeptide products encoded thereby, i.e., mammalian DGAT2α, and methods for producing the same, are provided. Also provided are: methods and compositions for modulating DGAT2α activity, e.g. in the treatment of disease conditions associated with DGAT2α activity, including obesity; DGAT2α transgenic cells, animals, plants and fungi, and methods for their preparation, e.g. for use in research, food production, industrial feedstock production, etc.; and methods for making triglycerides and triglyceride compositions, e.g. oils. The methods and compositions of the subject invention find use in a variety of different applications and fields, including research, medicine, agriculture and industry.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Nucleic Acid Compositions

Nucleic acid compositions encoding polypeptide products, as well as fragments thereof, having diglyceride acetyltransferase activity are provided. Specifically, nucleic acid compositions encoding mammalian, e.g., human, mouse, etc., DGAT2α polypeptides having diglyceride acyltransferase activity are provided. By nucleic acid composition is meant a composition comprising a sequence of DNA having an open reading frame that encodes a DGAT2α polypeptide, i.e. a gene or genomic region encoding a polypeptide having diglyceride acyltransferase activity, and is capable, under appropriate conditions, of being expressed as a DGAT2α polypeptide. Also encompassed in this term are nucleic acids that are homologous or substantially similar or identical to the nucleic acids encoding DGAT2α polypeptides or proteins. Thus, the subject invention provides nucleic acids encoding mammalian DGAT2α, such as nucleic acids encoding human DGAT2α and homologs thereof and mouse DGAT2α and homologs thereof. The coding sequence of the human DGAT2α genomic sequence, i.e. the human cDNA encoding the human DGAT2α enzyme, includes or comprises a nucleic acid sequence substantially the same as or identical to that identified as SEQ ID NO:01, infra. The coding sequence of the mouse DGAT2α genomic sequence, i.e., the mouse cDNA encoding the mouse DGAT2α enzyme, includes or comprises a nucleic acid substantially the same as or identical to the sequence identified as SEQ ID NO:03, infra.

The source of homologous nucleic acids to those specifically listed above may be any species, including both animal and plant species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10. Unless specified otherwise, all sequence identity values provided herein are determined using GCG (Genetics Computer Group, Wisconsin Package, Standard Settings, gap creation penalty 3.0, gap extension penalty 0.1). The sequences provided herein are essential for recognizing DGAT2α—related and homologous polynucleotides in database searches. Specific DGAT2α homologues of interest are provide in FIG. 8, i.e., SEQ ID NOs. 05, 07, 09, 11, 13 and 15.

Also provided are nucleic acids that hybridize to the above described specific nucleic acids, e.g., those nucleic acids having a sequence of SEQ ID NO:01 or 03, under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sneared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

Nucleic acids encoding the DGAT2α proteins and DGAT2α polypeptides of the subject invention may be cDNAs or genomic DNAs, i.e. portions of chromosomes that include both introns and exons, as well as promoter regions, etc., as well as fragments thereof. The term "DGAT2α—gene" shall be intended to mean the open reading frame encoding specific DGAT2α proteins and polypeptides, and DGAT2α introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a DGAT2α protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject DGAT2α proteins and polypeptides, described in greater detail infra. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The DGAT2α—nucleic acids or genes of the subject invention are isolated and obtained in substantial purity, generally as other than an intact chromosome. Usually, the DNA will be obtained substantially free of other nucleic acid sequences that do not include a DGAT2α sequence or fragment thereof, generally being at least about 50%, usually at least about 90% pure and are typically "recombinant", i.e. flanked by one or more nucleotides with which it is not normally associated on a naturally occurring chromosome.

In addition to the plurality of uses described in greater detail in following sections, the subject nucleic acid compositions find use in the preparation of all or a portion of the DGAT2α polypeptides, as described below.

Polypeptide Compositions

Also provided by the subject invention are DGAT2α polypeptides having diglyceride acyltransferase activity, i.e., capable of catalyzing the acylation of diacylglycerol. The term polypeptide composition as used herein refers to both full length proteins as well as portions or fragments thereof. Also included in this term are variations of the naturally occurring proteins, where such variations are homologous or substantially similar to the naturally occurring protein, as described in greater detail below, be the naturally occurring protein the human protein, mouse protein, or protein from some other mammalian species which naturally expresses a DGAT2α enzyme. In the following description of the subject invention, the term DGAT2α is used to refer not only to the human form of the enzyme, but also to homologs thereof expressed in non-human mammalian species.

The subject DGAT2α proteins are, in their natural environment, trans-membrane proteins. The subject proteins are characterized by the presence of at least one potential N-linked glycosylation site, at least one potential tyrosine phosphorylation site, and multiple hydrophobic domains, including 4 to 12, e.g., 6, hydrophobic domains capable of serving as trans-membrane regions. The proteins range in length from about 300 to 500, usually from about 325 to 475 and more usually from about 350 to 425 amino acid residues, and the projected molecular weight of the subject proteins based solely on the number of amino acid residues in the protein ranges from about 35 to 55, usually from about 37.5 to 47.5 and more usually from about 40 to 45 kDa, where the actual molecular weight may vary depending on the amount of glycolsylation of the protein and the apparent molecular weight may be considerably less because of SDS binding on gels.

The amino acid sequences of the subject proteins are characterized by having substantially no homology to the known DGAT enzymes. More specifically, the subject human DGAT2α enzymes have substantially no homology to the human DGAT enzyme described in Cases et al., "Identification of a gene encoding an acyl CoA:diacylglycerol acyltransferase, a key enzyme in triacylglycerol synthesis," Proc. Natl. Acad. Sci. U.S.A. 95 (22), 13018-13023 (1998). Likewise, the subject mouse DGAT2α enzymes have substantially no homology to the mouse DGAT enzyme described in Cases et al., "Identification of a gene encoding an acyl CoA:diacylglycerol acyltransferase, a key enzyme in triacylglycerol synthesis," Proc. Natl. Acad. Sci. U.S.A. 95 (22), 13018-13023 (1998). By substantially no homology is meant that the homology does not exceed about 20%, and usually will not exceed about 10% and more usually will not exceed about as determined using GCG (Genetics Computer Group, Wisconsin Package, Standard Settings, Gap Creation Penalty 3.0, Gap Extension Penalty 0.1).

Of particular interest in many embodiments are proteins that are non-naturally glycosylated. By non-naturally glycosylated is meant that the protein has a glycosylation pattern, if present, which is not the same as the glycosylation pattern found in the corresponding naturally occurring protein. For example, human DGAT2α of the subject invention and of this particular embodiment is characterized by having a glycosylation pattern, if it is glycosylated at all, that differs from that of naturally occurring human DGAT2α. Thus, the non-naturally glycosylated DGAT2α proteins of this embodiment include non-glycosylated DGAT2α proteins, i.e. proteins having no covalently bound glycosyl groups.

The sequence of the full length human DGAT2α protein is identified, infra, as SEQ ID NO:02. As such, DGAT2α proteins having an amino acid sequence that is substantially the same as or identical to the sequence of SEQ ID NO:2 are of interest. By substantially the same as is meant a protein having a region with a sequence that has at least about 75%, usually at least about 90% and more usually at least about 98% sequence identity with the sequence of SED ID NO:02, as measured by GCG, supra. Of particular interest in other embodiments is the mouse DGAT2α protein, where the mouse DGAT2α protein of the subject invention has an amino acid sequence that is substantially the same as or identical to the sequence appearing as SEQ ID NO:04, infra.

In addition to the specific mammalian DGAT2α proteins described above, homologs or proteins (or fragments thereof) from other species, i.e. other animal or plant species, are also provided, where such homologs or proteins may be from a variety of different types of species, including animals, such as mammals, e.g., rodents, such as rats, mice; domestic animals, e.g. horse, cow, dog, cat; humans, and the like. By homolog is meant a protein having at least about 35%, usually at least about 40% and more usually at least about 60% amino acid sequence identity the specific DGAT2α proteins as identified in SEQ ID NOS: 02 to 04, where sequence identity is determined using GCG, supra. Specific homologs of interest include human DC 2, human DC3, human DC4, human DC5, mouse DC2 and mouse DC3, the sequences of which are provided in FIG. 8 (i.e., SEQ ID NOs. 06, 08, 10, 12, 14 and 16).

The DGAT2α proteins of the subject invention (e.g. human DGAT2α or a homolog thereof; non-human DGAT2α proteins, e.g. mouse DGAT2α are present in a non-naturally occurring environment, e.g. are separated from their naturally occurring environment. In certain embodiments, the subject DGAT2α is present in a composition that is enriched for DGAT2α as compared to DGAT2α in its naturally occurring environment. As such, purified DGAT2α is provided, where by purified is meant that DGAT2α is present in a composition that is substantially free of non DGAT2α proteins, where by substantially free is meant that less than 90%, usually less than 60% and more usually less than 50% of the composition is made up of non-DGAT2α proteins. For compositions that are enriched for DGAT2α proteins, such compositions will exhibit a DGAT2α activity of at least about 100, usually at least about 200 and more usually at least about 1000 pmol triglycerides formed/mg protein/min, where such activity is determined by the assay described in the Experimental Section, infra.

In certain embodiments of interest, the DGAT2α protein is present in a composition that is substantially free of the constituents that are present in its naturally occurring environment. For example, a human DGAT2α protein comprising composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's constituents will still be present in the composition prepared from the naturally occurring source.

The DGAT2α of the subject invention may also be present as an isolate, by which is meant that the DGAT2α is substantially free of both non-DGAT2α proteins and other naturally occurring biologic molecules, such as oligosaccharides, polynucleotides and fragments thereof, and the like, where substantially free in this instance means that less than 70%, usually less than 60% and more usually less than 50% (dry weight) of the composition containing the isolated DGAT2α is a non-DGAT naturally occurring biological molecule. In certain embodiments, the DGAT2α is present in substantially pure form, where by substantially pure form is meant at least 95%, usually at least 97% and more usually at least 99% pure.

In addition to the naturally occurring DGAT2α proteins, DGAT2α polypeptides which vary from the naturally occurring DGAT2α proteins are also provided. By DGAT2α polypeptides is meant proteins having an amino acid sequence encoded by an open reading frame (ORF) of a DGAT2α gene, described supra, including the full length DGAT2α protein and fragments thereof, particularly biologically active fragments and/or fragments corresponding to functional domains; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to a DGAT2α protein of SEQ ID NO:2, SEQ ID NO:04, or a homolog thereof, of at least about 10 aa, and usually at least about 15 aa, and in many embodiments at least about 50 aa in length.

Preparation of DGAT2α Polypeptides

The subject DGAT2α proteins and polypeptides may be obtained from naturally occurring sources, but are preferably synthetically produced. Where obtained from naturally occurring sources, the source chosen will generally depend on the species from which the DGAT2α is to be derived.

The subject DGAT2α polypeptide compositions may be synthetically derived by expressing a recombinant gene encoding DGAT2α, such as the polynucleotide compositions described above, in a suitable host. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a DGAT2α gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

DGAT2α proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the DGAT2α coding sequence in eukaryotic cells, where the DGAT2α protein will benefit from native folding and post-translational modifications. Small peptides can also be synthesized in the laboratory. Polypeptides that are subsets of the complete DGAT2α sequence may be used to identify and investigate parts of the protein important for function.

Once the source of the protein is identified and/or prepared, e.g. a transfected host expressing the protein is prepared, the protein is then purified to produce the desired DGAT2α comprising composition. Any convenient protein purification procedures may be employed, where suitable protein purification methodologies are described in Guide to Protein Purification, (Deuthser ed.) (Academic Press, 1990). For example, a lysate may prepared from the original source, e.g. naturally occurring cells or tissues that express DGAT2α or the expression host expressing DGAT2α, and purified using HPLC, exclusion chromatography, gel electrophoresis, affinity chromatography, and the like.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (USA) (1983) 80:21-25; and Siebenlist et al., *Cell* (1980) 20:269.

Yeast. Expression systems in yeast include those described in Hinnen et al., *Proc. Natl. Acad. Sci.* (USA) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al.; *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilbum et al., *Gene* (1983) 26:205-221; Yelton et al., *Proc. Natl. Acad. Sci.* (USA) (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (USA) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (USA) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat.

Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence as disclosed in U.S. Pat. No. 5,641,670.

Methods and Compositions Having Research Application

Also provided by the subject invention are methods and compositions having research applications, such as in the study of the acylglycerol metabolism, in the identification of key components of the triglyceride synthesis pathway, in the identification of triglyceride synthesis modulatory agents, e.g. DGAT2α inhibitors or enhancers, and the like.

The subject nucleic acid compositions find use in a variety of research applications. Research applications of interest include: the identification of DGAT2α homologs; as a source of novel promoter elements; the identification of DGAT2α expression regulatory factors; as probes and primers in hybridization applications, e.g. PCR; the identification of expression patterns in biological specimens; the preparation of cell or animal models for DGAT2α function; the preparation of in vitro models for DGAT2α function; etc. Homologs of the specifically disclosed DGAT2α nucleic acids are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/0.15 mM sodium citrate). Nucleic acids having a region of substantial identity to the provided nucleic acid sequences bind to the provided sequences under stringent hybridization conditions. By using probes, particularly labeled probes of DNA sequences, one can isolate homologous or related genes. One can also use sequence information derived from the polynucleotide compositions of the subject invention to prepare electronic "probes" for use in searching of computer based sequence date, e.g. BLAST searches EST databases.

The sequence of the 5' flanking region of the subject nucleic acid compositions may be utilized as a source for promoter elements, including enhancer binding sites, that provide for developmental regulation in tissues where DGAT2α is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194-205; Mortlock et al. (1996), *Genome Res.* 6:327-33; and Joulin and Richard-Foy (1995), *Eur. J. Biochem.* 232:620-626.

The regulatory sequences may be used to identify cis acting sequences required for transcriptional or translational regulation of DGAT2 gene expression, especially in different tissues or stages of development, and to identify cis acting sequences and trans-acting factors that regulate or mediate DGAT2 gene expression. Such transcription or translational control regions may be operably linked to a DGAT2 gene in order to promote expression of wild type or altered DGAT2 or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of DGAT2α gene expression in the sample.

The sequence of a DGAT2α gene or nucleic acid, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated genes may be used to study structure-function relationships of DGAT2α, or to alter properties of the protein that affect its function or regulation.

The subject nucleic acids can be used to generate transgenic hosts, e.g non-human animals, such as mice, cows, rats, pigs etc., or site specific gene modifications in cell lines. Examples of transgenic hosts include hosts in which the naturally expressed DGAT2α gene has been disrupted, e.g. DGAT2α knock-outs, as well as hosts in which DGAT2α expression has been amplified, e.g. through introduction of additional DGAT2α copies, through introduction of strong promoter upstream of the DGAT2α gene, and the like. Using the nucleic acid compositions of the subject invention, standard protocols known to those of skill in the art may be used to produce such transgenic hosts that have been genetically manipulated with respect to the DGAT2α gene, i.e. DGAT2α transgenic hosts.

Transgenic animals may be made through homologous recombination, where the normal DGAT2α locus is altered, e.g. as in DGAT2α knockouts. Alternatively, a nucleic acid construct is randomly integrated into the genome. Vectors for stable integration include plasmids, retroviruses and other animal viruses, YACs; and the like. DNA constricts for homologous recombination will comprise at least a portion of the DGAT2α gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

For embryonic stem (ES) cells, an ES cell line may be employed, or embryonic cells may be obtained freshly from a host, e.g. mouse, rat, guinea pig, cow, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The resultant chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275-295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation. With *Agrobacterium* mediated transformation, co-integrative or binary vectors comprising the exogenous DNA are prepared and then introduced into an appropriate *Agrobacterium* strain, e.g. *A. tumefaciens*. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

The modified cells, animals or plants are useful in the study of DGAT2α function and regulation. For example, a series of small deletions and/or substitutions may be made in the host's native DGAT2α gene to determine the role of different exons in various physiological processes. Specific constructs of interest include anti-sense DGAT2α, which will block DGAT2α expression, expression of dominant negative DGAT2α mutations, and over-expression of DGAT2α genes.

Where a DGAT2α sequence is introduced, the introduced sequence may be either a complete or partial sequence of a DGAT2α gene native to the host, or may be a complete or partial DGAT2α sequence that is exogenous to the host animal, e.g., a human DGAT2α sequence. A detectable marker, such as lac Z may be introduced into the DGAT2α locus, where upregulation of DGAT2α gene expression will result in an easily detected change in phenotype. One may also provide for expression of the DGAT2α gene or variants thereof in cells or tissues where it is not normally expressed, at levels not normally present in such cells or tissues, or at abnormal times of development. The transgenic hosts, e.g. animals, plants, etc., may be used in functional studies, drug screening, etc., e.g. to determine the effect of a candidate drug on DGAT2α activity, to identify drugs that reduce serum triglyceride levels, etc.

The subject polypeptide compositions can be used to produce in vitro models of triglyceride synthesis, where such models will consist of the subject DGAT2α proteins and other components of triglyceride synthesis, e.g. substrates, such as diacylglycerol or metabolic precursors thereof, fatty acyl CoAs and the like, other components of the triacylglycerol synthetase complex, e.g. acyl CoA ligase, acyl CoA acyltransferase, monoacyl glycerol acyltransferase, etc.

Also provided by the subject invention are screening assays designed to find modulatory agents of DGAT2α activity, e.g. inhibitors or enhancers of DGAT2α activity, as well as the agents identified thereby, where such agents may find use in a variety of applications, including as therapeutic agents, as agricultural chemicals, etc. The screening methods will typically be assays which provide for qualitative/quantitative measurements of DGAT2α activity in the presence of a particular candidate therapeutic agent. For example, the assay could be an assay which measures the acylation activity of DGAT2α in the presence and absence of a candidate inhibitor agent. The screening method may be an in vitro or in vivo format, where both formats are readily developed by those of skill in the art. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product. Where in vitro assays are employed, the various components of the in vitro assay, e.g. the substrate, the donor, the DGAT2α protein and the candidate inhibitor, etc. are combined in a assay mixture under conditions sufficient for DGAT2α activity to occur, as described in the experimental section, infra.

A variety of other reagents may be included in the screening assay and reaction mixture. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Using the above screening methods, a variety of different therapeutic agents may be identified. Such agents may target the enzyme itself, or an expression regulator factor thereof. Such agents may inhibitors or promoters of DGAT2α activity, where inhibitors are those agents that result in at least a reduction of DGAT2α activity as compared to a control and enhancers result in at least an increase in DGAT2α activity as compared to a control. Such agents may be find use in a variety of therapeutic applications, as described in greater detail below.

Methods and Compositions Having Medical Applications

The methods and compositions of the subject invention also have broad ranging applications in a variety of medical applications, including diagnostic screening, therapeutic treatments of pathological conditions, in the regulation of DGAT2α activity in desirable ways, and the like.

The subject invention provides methods of screening individuals for a predisposition to a disease state or the presence of disease state, where such screening may focus on the presence of one or more markers, such as a mutated DGAT2α gene or expression regulatory element thereof, observed levels of DGAT2α; the expression level of the DGAT2α gene in a biological sample of interest; and the like.

Samples, as used herein, include biological fluids such as blood, cerebrospinal fluid, tears, saliva, lymph, semen, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal DGAT2α in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of DGAT2α encoding nucleic acids. Biochemical studies may be performed to determine whether a sequence polymorphism in a DGAT2α coding region or control regions is associated with disease. Disease associated polymorphisms may include deletion or truncation of the gene, mutations that alter expression level, that affect the activity of the protein, etc.

Changes in the promoter or enhancer sequence that may affect expression levels of DGAT2α can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express DGAT2α may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type DGAT2α sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in DGAT2α may be based on the functional or antigenic characteristics of the protein. Protein truncation assays are useful in detecting deletions that may affect the biological activity of the protein. Various immunoassays designed to detect polymorphisms in DGAT2α proteins may be used in screening. Where many diverse genetic mutations lead to a particular disease phenotype, functional protein assays have proven to be effective screening tools. The activity of the encoded DGAT2α protein may be determined by comparison with the wild-type protein.

Diagnostic methods of the subject invention in which the level of DGAT2α expression is of interest will typically involve comparison of the DGAT2α nucleic acid abundance of a sample of interest with that of a control value to determine any relative differences, where the difference may be measured qualitatively and/or quantitatively, which differences are then related to the presence or absence of an abnormal DGAT2α expression pattern. A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

The subject diagnostic or screening methods may be used to identify the presence of, or predisposition to, disease conditions associated with acylglycerol metabolism, particularly those associated with DGAT2α activity. Such disease conditions include: hyperlipidemia (including excess serum triglyceride levels), cardiovascular disease, obesity, diabetes, cancer, neurological disorders, immunological disorders, and the like.

Also provided are methods of regulating, including enhancing and inhibiting, DGAT2α activity in a host. A variety of situations arise where modulation of DGAT2α activity in a host is desired, where such conditions include disease conditions associated with DGAT2α activity and non-disease conditions in which a modulation of DGAT2α activity is desired for a variety of different reasons, e.g. cosmetic weight control.

For the modulation of DGAT2α activity in a host, an effective amount of active agent that modulates the activity, e.g. reduces the activity, of DGAT2α in vivo, is administered to the host. The active agent may be a variety of different compounds, including: the polynucleotide compositions of the subject invention, the polypeptide compositions of the subject invention, a naturally occurring or synthetic small molecule compound, an antibody, fragment or derivative thereof, an antisense composition, and the like.

The nucleic acid compositions of the subject invention find use as therapeutic agents in situations where one wishes to enhance DGAT2α activity in a host, e.g. in a mammalian host in which DGAT2α activity is low resulting in a disease condition, etc. The DGAT2αgenes, gene fragments, or the encoded DGAT2α protein or protein fragments are useful in gene therapy to treat disorders associated with DGAT2α defects. Expression vectors may be used to introduce the DGAT2α gene or encoding nucleic acid into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Of particular interest are those agents identified by the screening assays of the subject invention, as described above.

Also of interest as active agents are antibodies that modulate, e.g. reduce, if not inhibit, DGAT2α activity in the host. Suitable antibodies are obtained by immunizing a host animal with peptides comprising all or a portion of a DGAT protein, such as the DGAT2α polypeptide compositions of the subject invention. Suitable host animals include mouse, rat sheep, goat, hamster, rabbit, etc. The origin of the protein immunogen may be mouse, human, rat, monkey etc. The host animal will generally be a different species than the immunogen, e.g. human DGAT used to immunize mice, etc.

The immunogen may comprise the complete protein, or fragments and derivatives thereof. Preferred immunogens comprise all or a part of DGAT2α, where these residues contain the post-translation modifications, such as glycosylation, found on the native DGAT2α. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with DGAT2α, where the DGAT2α will preferably be in substantially pure form, comprising less than about 1% contaminant. The immunogen may comprise complete DGAT2α, fragments or derivatives thereof. To increase the immune response of the host animal, the DGAT may be combined with an adjuvant, where suitable adjuvants include alum, dextran, sulfate, large polymeric anions, oil & water emulsions, e.g. Freund's adjuvant, Freund's complete adjuvant, and the like. The DGAT2α may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The DGAT2α is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using DGAT2α bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig pro noters, etc.

In yet other embodiments of the invention, the active agent is an agent that modulates, and generally decreases or down regulates, the expression of DGAT2α encoding nucleic acids in the host. Antisense molecules can be used to down-regulate expression of these target nucleic acids in cells. The antisense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

As mentioned above, an effective amount of the active agent is administered to the host, where "effective amount" means a dosage sufficient to produce a desired result, where the desired result in the desired modulation, e.g. enhancement, reduction, of DGAT2α activity.

In the subject methods, the active agent(s) may be administered to the host using any convenient means capable of resulting in the desired effect. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules; powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulations to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DGAT DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving acylglycerol metabolism, and particularly DGAT2α activity, including both insufficient or hypo-DGAT2α activity and hyper-DGAT2α activity. Representative diseases that may be treated according to the subject methods include: hyperlipidemia (including excess serum triglyceride levels), cardiovascular disease, obesity, diabetes, cancer, neurological disorders, immunological disorders, skin disorders associated with sebaceous gland activity, e.g. acne, and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as serum triglyceride level, weight, total body fat content, etc. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. For example, where the disease condition is marked by the presence of elevated lipid levels, treatment includes at least a reduction in the observed lipid levels, including a restoration of normal lipid levels. As another example, where the disease is obesity, treatment results in at least a reduction in the overall weight and/or total body fat content of the host.

The subject methods also find use in the modulation of DGAT2α activity in hosts not suffering from a disease condition but in which the modulation of DGAT2α activity is nonetheless desired. For example, sperm production in males has been associated with diglyceride acyltransferase activity. As such, in males where at least reduced sperm production is desired, the subject methods can be used to reduce this target activity in such males, e.g. by administering an agent that reduces DGAT2α activity in such males, where such agents are described above. In other words, the subject methods provide a means of male contraception. Alternatively, where increased sperm count in a given male is desired, e.g. in those conditions where the male has reduced fertility, the subject methods can be used to enhance this target activity in the male and thereby increase sperm count and fertility, e.g. by administering to the male host a DGAT2α enhancing agent, as described above.

A variety of hosts are treatable according to the subject methods. Generally such hosts are "mammals" or "mamrmalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods and Compositions for Producing Triglycerides and Triglyceride Compositions Also provided by the subject invention are methods for preparing triglycerides and triglyceride comprising compositions, as well as the compositions produced by these methods. In preparing-triglycerides with the subject invention, at least the direct substrates of the desired triacylglyercol, e.g. diacylglycerol and fatty acyl CoA, will be combined in the presence of the polypeptide under conditions sufficient for the acylation of the diacylglycerol to occur. The synthesis may occur in an in vitro system, e.g. in a vessel in which the substrates or precursors thereof and the DGAT2α enzyme, as well as any other requisite enzymes (e.g. as need to convert the substrate precursors to substrates), or an in vivo system, e.g. a host cell that naturally comprises the substrates and into which a DGAT2α gene or nucleic acid according to the subject invention has been inserted in a manner sufficient for expression of the gene and provision of the DGAT2α enzyme, where the resultant triglyceride products may be separated from the host cell using standard separation techniques.

Of interest for use in producing triglyceride compositions are transgenic plants/fungi that have been genetically manipulated using the nucleic acid compositions of the subject invention to produce triglycerides and/or compositions thereof in one or more desirable ways. Transgenic plants/fungi of the subject invention are those plants/fungi that at least: (a) produce more triglyceride or triglyceride composition than wild type, e.g. produce more oil, such as by producing seeds having a higher oil content, as compared to wild-type; (b) produce triglyceride compositions, e.g. oils, that are enriched for triglycerides and/or enriched for one or more particular triglycerides as compared to wild type; and the like. Of interest are transgenic plants that produce commercially valuable triglyceride compositions or oils, such as canola, rapeseed, palm, corn, etc., containing various poly- and mono-unsaturated fatty acids, and the like. Of particular interest are transgenic plants, such as canola, rapeseed, palm, oil, etc., which have been genetically modified to produce seeds having higher oil content than the content found in the corresponding wild type, where the oil content of the seeds produced by such plants is at least 10% higher, usually at least 20% higher, and in many embodiments at least 30% higher than that found in the wild type, where in many embodiments seeds having oil contents that are 50% higher, or even greater, as compared to seeds produced by the corresponding wild-type plant, are produced. The seeds produced by such DGAT2α transgenic plants can be used as sources of oil or as sources of additional DGAT2α transgenic plants. Such transgenic plants and seeds therefore find use in methods of producing oils. In such methods, DGAT2α transgenic plants engineered to produce seeds having a higher oil content than the corresponding wild-type, e.g. seeds in which the DGAT2α gene is overexpressed, are grown, the seeds are harvested and then processed to recover the oil. The subject transgenic plants can also be used to produce novel oils characterized by the presence of triglycerides in different amounts and/or ratios than those observed in naturally occurring oils. The transgenic plants/fungi described above can be readily produced by those of skill in the art armed with the nucleic acid compositions of the subject invention. See the discussion on how to prepare transgenic plants, supra.

The triglyceride compositions described above find use in a variety of different applications. For example, such compositions or oils find use as food stuffs, being used as ingredients, spreads, cooking materials, etc. Alternatively, such oils find use as industrial feedstocks for use in the production of chemicals, lubricants, surfactants and the like.

Also of interest are transgenic non-human animals suitable for use as sources of food products and/or animal based industrial products. Such trans-genic non-human animals, e.g. transgenic mice, rats, livestock, such as cows, pigs, horses, birds, etc, may be produced using methods known in the art and reviewed supra. Such trans-genic non-human animals can be used for sources of a variety of different food and industrial products in which the triglyceride content is specifically tailored in a desirable manner. For example, such transgenic animals that have been modified in a manner such that DGAT2α activity is reduced as compared to the wild type can be used as sources of food products that are low in triglyceride content, e.g. low fat or lean meat products, low fat milk, low fat eggs, and the like.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

Experimental

I. Existence of DGAT2α

A. Mice (DGAT1−/−) lacking DGAT, as described in WO 99/67268 are lean and resistant to diet-induced obesity, but are still capable of synthesizing triglycerides (TG) and have normal plasma TG levels. However, DGAT activity is virtually absent in membrane preparations from DGAT1−/− tissues (Smith et al., Nat. Genet. 2000 (25), 87-90). Using pulse assays in living cells, we measured that the residual TG synthesis activity in DGAT1−/− Mouse Embryonic Fibroblasts (MEF) or adipocytes was about 40% of that in wild-type cells. The results are graphically depicted in FIGS. 1A and 1B. In FIG. 1A the membrane fraction isolated from MEF or adipocytes of wild-type or DGAT1−/− mice was used as the enzyme source in DGAT assays in vitro. In FIG. 1B living cells were pulse-labeled with [$^{14}$C]oleic acid for 24 hours and [$^{14}$C] incorporation in the TG fraction was measured.

In further assays, increased DGAT activity was observed in DGAT1−/− membranes assayed without magnesium; and DGAT activity was observed to vary with magnesium concentration in liver and adipose tissue.

The above findings indicate the existence of DGAT2α, a second enzyme with diglyceride acyltransferase activity.

II. Mammalian DGAT2α Sequences

A. The human DGAT2α nucleic acid and amino acid sequences were identified using standard procedures, as described above. The human DGAT2α cDNA has the sequence appearing as SEQ ID NO:01, infra, while the protein encoded thereby has the sequence appearing as SEQ ID NO:02, infra.

B. The mouse DGAT2α nucleic acid and amino acid sequences were identified using standard procedures, as described above. The mouse DGAT2α cDNA has the sequence appearing as SEQ ID NO:03, infra, while the protein encoded thereby has the sequence appearing as SEQ ID NO:04, infra.

II. Characterization of DGAT2α

A. Molecular Weight

The mouse DGAT2α cDNA was determined to encode a 43 kD predicted protein based on the amino acid sequence. The mouse DGAT2α cDNA was determined to have no sequence homology to DGAT1, as described in Cases et al., supra. The mouse DGAT2α amino acid sequence was determined to have 2 putative N-linked glycosylation sites. The mouse DGAT2α amino acid sequence was determined to have 6 putative PKC phosphorylation sites. A Hydrophobicity plot assessed by Kyte-Doolittle (K-D) analysis revealed the existence of multiple putative transmembrane domains in the mouse DGAT2α amino acid sequence. FIG. 2 provides a graphical result of this analysis. As such, there are regions of higher hydrophobicity compatible with the existence of one or more transmembrane domain.

III. Further Characterization

A. Expression of DGAT2α in Insect Cells

Figure 3A:
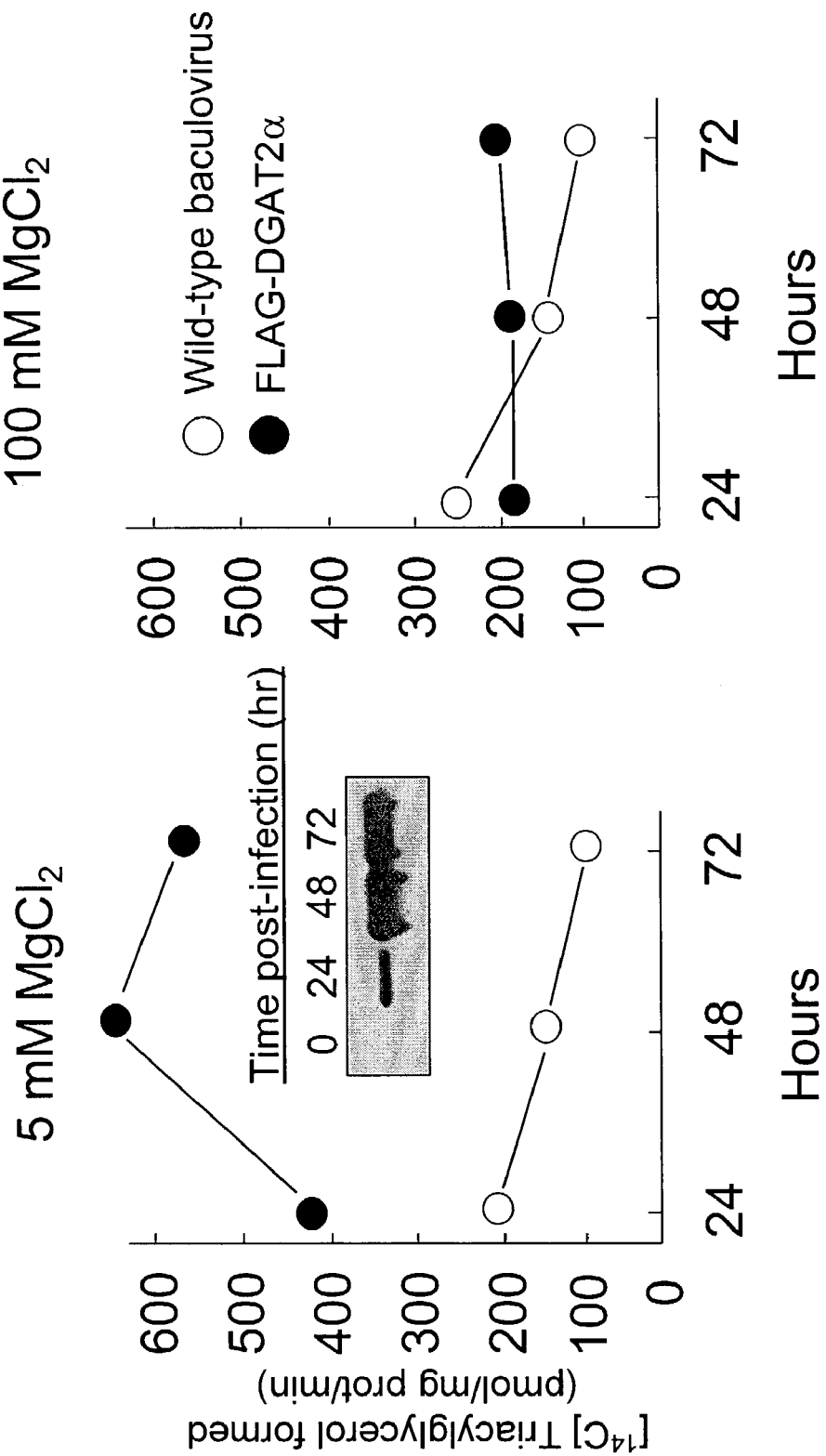

Sf9 insect cells were infected with wild-type baculovirus, mouse FLAG-tagged DGAT2α or mouse FLAG-tagged DGAT1 (Cases et al., supra) recombinant baculoviruses, and the membrane fractions were assayed for DGAT activity. The results are graphically provided in FIG. 3A. In FIG. 3A a time course of DGAT2α virus infection is provided. Insect cell membranes were isolated at the indicated times after infection. Expression of the FLAG-tagged DGAT2α protein was detected by immunoblotting with an anti-FLAG antibody (Inset). DGAT activity was measured at low (5 mM) or high (100 mM) magnesium concentration, using [$^{14}$C]oleoyl CoA and cold diacylglycerol. The experiment was repeated three times and a representative experiment is shown. FIG. 3B shows that DGAT2α activity is dependent on the presence of the diacylglycerol substrate. Assays were performed at low magnesium concentration, using [14$^C$]oleoyl CoA with or without exogenous cold diacylglycerol. When no diacylglycerol is added, no significant DGAT activity can be detected over background. Data represent the mean (±SD) of three experiments. To compare the DGAT activity of DGAT1 and DGAT2α, membranes expressing equal levels of DGAT1 or DGAT2α (as assessed by immunoblotting with an anti-FLAG antibody) were assayed at low magnesium concentration using increased amounts of cold oleoyl CoA in the presence of exogenous diacylglycerol. The results are provided in FIG. 3C. Lipids were extracted and separated by TLC and TG accumulation was visualized by charring and quantified by densitometry.

B. Analysis of DGAT2α mRNA Expression Mouse DGAT2α mRNA Expression was Analyzed. The Results are Provided in FIG. 4.

C. DGAT2α Expression Increases During 3T3-L1 Adipocyte Differentiation

Figure 5:
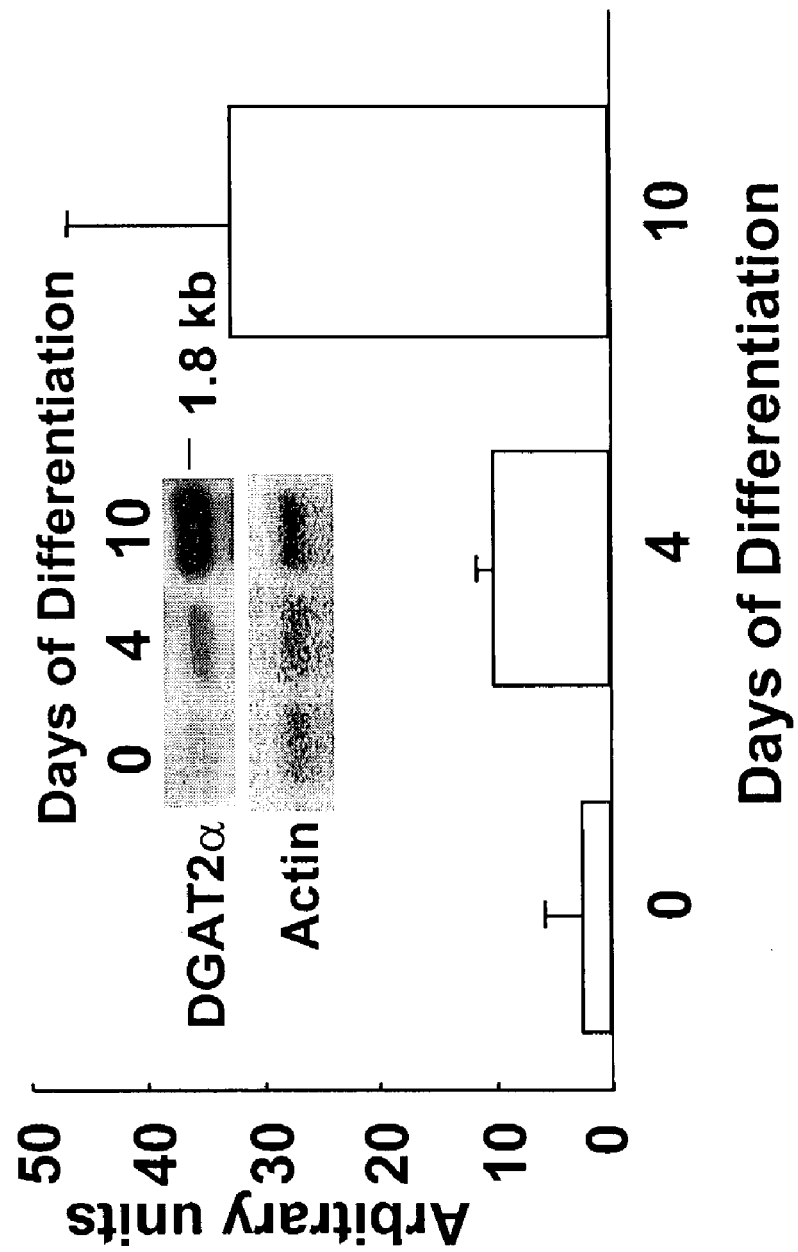
FIG. 5 provides the results of an assay showing that mouse DGAT2α expression increases during 3T3-L1 adipocyte differentiation.

Mouse 3T3-L1 adipocyte differentiation was induced and mRNA were isolated at the indicated times shown in FIG. 5. Quantitation of DGAT2α mRNA levels in triplicate samples was perfromed by Phosphorimager analysis and corrected for loading relative to actin expression. The results are shown in FIG. 5.

IV. Summary of DGAT2α mouse DGAT2α has no sequence homology to DGAT1
mouse DGAT2α diacylglycerol acyltransferase activity inhibited by high magnesium concentrationsm;
mouse DGAT2α RNA expression in many tissues, highest levels found in liver, adipose tissue, and mammary gland
mouse DGAT2α markedly increased mRNA expression during 3T3-L1 adipocyte differentiation.

It is apparent from the above results and discussion that polynucleotides encoding mammalian DGAT2α enzymes, as well as novel polypeptides encoded thereby, are provided. The subject invention is important for both research and therapeutic applications. Using the DGAT2α probes of the subject invention, the role of DGAT2α and its regulation in a number of physiological processes can be studied in vivo. The subject invention also provides for important new ways of treating diseases associated with DGAT2α, such as hypertriglycemia and obesity, as well as in the production of tryglycerides.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for inhibiting the diacylglycerol O-acyltransferase activity of a diacylglycerol acyltransferase-2α (DGAT2α) protein, said method comprising:
   a) measuring diacylglycerol acyltransferase activity of said DGAT2α protein; and
   b) contacting said DGAT2α protein with an antibody that inhibits the diacylglycerol O-acyltransferase activity of said DGAT2α protein, wherein the DGAT2α protein comprises an amino acid sequence having at least about 98% identity to the amino acid sequence set forth in SEQ ID NO:2.

2. The method of claim 1, wherein said antibody is a monoclonal antibody.

* * * * *

UNITED STATES PATENT AND TRADEMARK OFFICE
CERTIFICATE OF CORRECTION

PATENT NO.        : 7,862,819 B2                                       Page 1 of 1
APPLICATION NO.   : 10/446441
DATED             : January 4, 2011
INVENTOR(S)       : Sylvaine Cases It is certified that error appears in the above-identified patent and that said Letters Patent is hereby corrected as shown below:

Please replace the Statement Regarding Federally Sponsored Research beginning on column 1, line 17, with the following revised statement:

STATEMENT REGARDING FEDERALLY SPONSORED RESEARCH
This invention was made with Government support under grant no. DK56084 awarded by the National Institutes of Health. The Government has certain rights in this invention.

Signed and Sealed this
Eighth Day of March, 2011

David J. Kappos
*Director of the United States Patent and Trademark Office*